(12) United States Patent
Qian et al.

(10) Patent No.: US 7,691,579 B2
(45) Date of Patent: Apr. 6, 2010

(54) METHODS AND COMPOSITIONS FOR PRODUCING AN ENHANCED IMMUNE RESPONSE TO A HUMAN PAPILLOMAVIRUS IMMUNOGEN

(75) Inventors: Jiahua Qian, Germantown, MD (US); Jay A. Berzofsky, Bethesda, MD (US); Samir N. Khleif, Silver Spring, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 73 days.

(21) Appl. No.: 11/918,557

(22) PCT Filed: Apr. 11, 2006

(86) PCT No.: PCT/US2006/013315

§ 371 (c)(1),
(2), (4) Date: Oct. 15, 2007

(87) PCT Pub. No.: WO2006/113209

PCT Pub. Date: Oct. 26, 2006

(65) Prior Publication Data

US 2009/0068214 A1 Mar. 12, 2009

Related U.S. Application Data

(60) Provisional application No. 60/671,463, filed on Apr. 15, 2005, provisional application No. 60/680,000, filed on May 12, 2005, provisional application No. 60/724,783, filed on Oct. 11, 2005.

(51) Int. Cl.
*C12Q 1/68* (2006.01)
(52) U.S. Cl. .......................................... 435/6
(58) Field of Classification Search ....................... 435/6
See application file for complete search history.

(56) References Cited

U.S. PATENT DOCUMENTS

| 4,258,029 | A | 3/1981 | Moloney et al. |
|---|---|---|---|
| 4,946,778 | A | 8/1990 | Ladner et al. |
| 5,098,843 | A | 3/1992 | Calvin |
| 5,139,941 | A | 8/1992 | Muzyczka et al. |
| 5,173,414 | A | 12/1992 | Lebkowski et al. |
| 5,219,740 | A | 6/1993 | Miller et al. |
| 5,225,539 | A | 7/1993 | Winter |
| 5,530,101 | A | 6/1996 | Queen et al. |
| 5,589,466 | A | 12/1996 | Felgner et al. |
| 5,612,207 | A | 3/1997 | Nicolau et al. |
| 5,620,896 | A | 4/1997 | Herrmann et al. |
| 5,641,665 | A | 6/1997 | Hobart et al. |
| 5,703,055 | A | 12/1997 | Felgner et al. |
| 5,707,812 | A | 1/1998 | Horn et al. |
| 5,720,921 | A | 2/1998 | Meserol |
| 5,846,846 | A | 12/1998 | Suh et al. |
| 5,861,397 | A | 1/1999 | Wheeler |
| 5,891,718 | A | 4/1999 | Hobart et al. |
| 6,013,262 | A | 1/2000 | Frazer et al. |
| 6,022,874 | A | 2/2000 | Wheeler |
| 6,074,605 | A | 6/2000 | Meserol et al. |
| 6,090,617 | A | 7/2000 | Meserol |
| 6,147,055 | A | 11/2000 | Hobart et al. |
| 6,214,804 | B1 | 4/2001 | Felgner et al. |
| 6,228,844 | B1 | 5/2001 | Wolff et al. |
| 6,399,588 | B1 | 6/2002 | Hobart et al. |
| 6,413,942 | B1 | 7/2002 | Felgner et al. |
| 6,451,769 | B1 | 9/2002 | Huebner et al. |
| 6,485,961 | B1 | 11/2002 | Meserol |
| 6,562,351 | B2 | 5/2003 | Hallek et al. |
| 6,649,167 | B2 | 11/2003 | Hallek et al. |
| 6,835,550 | B1 | 12/2004 | Estell et al. |
| 6,838,269 | B1 | 1/2005 | Estell et al. |
| 6,878,541 | B2 | 4/2005 | Quia et al. |
| 6,897,049 | B1 | 5/2005 | Estell et al. |
| 7,026,443 | B1 * | 4/2006 | Sette et al. ................ 530/300 |
| 7,132,262 | B2 * | 11/2006 | Ertl et al. ................... 435/69.1 |
| 2002/0193565 | A1 | 12/2002 | Stanley et al. |
| 2003/0022860 | A1 * | 1/2003 | Melief et al. ................. 514/44 |
| 2003/0099644 | A1 | 5/2003 | Ahuja et al. |
| 2003/0129728 | A1 | 7/2003 | Qiao et al. |
| 2005/0181458 | A1 | 8/2005 | Harding et al. |

FOREIGN PATENT DOCUMENTS

| EP | 929536 | 7/1999 |
|---|---|---|
| EP | 1006796 | 6/2000 |
| EP | 1165140 | 1/2002 |

(Continued)

OTHER PUBLICATIONS

Schiller et al, Journal of Clinical Virology, 2000, vol. 19, pp. 67-74.*
Ahlers J.D. et al. 1997. "Enhanced immunogenicity of HIV-1 vaccine construct by modification of the native peptide sequence." *PNAS USA* 94:10856-10861.
Ahlers, J.D. et al. 2001. "Mechanisms of cytokine synergy essential for vaccine protection against viral challenge." *Int. Immunol.* 13:897-908.
Ahlers, J.D. et al. 2002. "A push-pull approach to maximize vaccine efficacy: abrogating suppression with an IL-13 inhibitor while augmenting help with granulocyte/macrophage colony-stimulating factor and CD40L." *PNAS USA* 99:13020-13025.
Banga, A.K. et al. "Assessing the potential of skin electroporation for the delivery of protein—and gene— based drugs", *Trends Biotechnol*,. vol. 16, pp. 408-412 (1998).
Banga, A.K. et al. "Iontophoresis and Electroporation: Comparisons and Contrasts", *Int J. Pharm.*, vol. 179, pp. 1-19 (1999).
Barbosa, M.S. et al. 1990. "The region of the HPV E7 oncoprotein homologous to adenovirus E1a and Sv40 large T antigen contains separate domains for Rb binding and casein kinase II phosphorylation." *EMBO J.* 9:153-160.

(Continued)

*Primary Examiner*—Ali R. Salimi
(74) *Attorney, Agent, or Firm*—Woodcock Washburn LLP

(57) ABSTRACT

The present invention relates to novel methods for producing an enhanced immune response to an immunogen in a subject via the co-administration of a CD40 agonist and a GM-CSF agent.

20 Claims, 21 Drawing Sheets

FOREIGN PATENT DOCUMENTS

| | | |
|---|---|---|
| WO | WO 92/01070 | 1/1992 |
| WO | WO 93/03769 | 3/1993 |
| WO | WO 94/20137 | 9/1994 |
| WO | WO 94/29469 | 12/1994 |
| WO | WO 95/29703 | 11/1995 |
| WO | WO 97/47197 | 6/1997 |
| WO | WO 98/14439 | 4/1998 |
| WO | WO 99/50424 | 10/1999 |
| WO | WO 99/61052 | 12/1999 |
| WO | WO 00/09699 | 2/2000 |
| WO | WO 00/35478 | 6/2000 |
| WO | WO 00/45841 A3 | 8/2000 |
| WO | WO 00/57917 | 10/2000 |
| WO | WO 00/73263 | 12/2000 |
| WO | WO 01/09303 | 2/2001 |
| WO | WO 02/92796 | 3/2002 |
| WO | WO 02/077012 | 10/2002 |
| WO | WO 03/028632 | 4/2003 |
| WO | WO 03/031583 | 4/2003 |
| WO | WO 03/077942 | 9/2003 |
| WO | WO 2004/052395 | 6/2004 |
| WO | WO 2004/056389 | 7/2004 |
| WO | WO 2005/026192 | 3/2005 |
| WO | WO 2005/032586 | 4/2005 |

OTHER PUBLICATIONS

Baur, M. et al. 2005. "Phase I/II study of oral etoposide plus GM-CSF as second-line chemotherapy in platinum-pretreated patients with advanced ovarian cancer." *Br. J. Cancer* 92:1019-1025.

Bett, et al. "Packaging capacity and stability of Human Adenovirus Type 5 vectors", *J. Virol.*, vol. 67, pp. 5911-5921 (1993).

Bodaghi et al. "Colorectal papillomavirus infection in patients with colorectal cancer", *Clin. Cancer Res.*, vol. 11, pp. 2862-2867 (2005).

Buck, C.B. et al. 2004. "Efficient intracellular assembly of papillomaviral vectors." *J. Virol.* 78:751-757.

Burns, et al. "Vesicular Stomatitis Virus G Glycoprotein pseudotyped retroviral vectors: Concentration to very high titer and efficient gene transfer into mammalian and nonmammalian cells", *Proc. Natl. Acad. Sci. USA*, vol. 90, pp. 8033-8037 (1993).

Canfield, et al. "The Binding affinity of Human IgG for its high Affinity Fc Receptor is determined by multiple Amino Acids in the Ch2 domain and is modulated by the hinge region", *J. Exp. Med.*, vol. 173, pp. 1483-1491 (1991).

Carter, B. J. " Adeno- Associated virus vectors", *Current Opin. Biotechnol.* vol. 3, pp. 533-539 (1992).

Chiodoni, C. et al. 1999. "Dendritic cells infiltrating tumors cotransduced with granulocyte/macrophage colony-stimulating factor (GM-CSF) and CD40 ligand genes take up and present endogenous tumor-associated antigens, and prime naive mice for a cytotoxic T lymphocyte response." *J. Exp. Med.* 190:125-133.

Costello, C.T. et al. "Iontophoresis: Applications in transdermal medication delivery", *Phys. Ther*, vol. 75, pp. 554-563 (1995).

Da Silva, D.M. et al. 2001 ."Physical interaction of human papillomavirus virus-like particles with immune cells." *Int. Immunol.* 13:633-641.

Da Silva, D.M. et al. 2003. "Heterologous boosting increases immunogenicity of chimeric papillomavirus virus-like particle vaccines." *Vaccine* 21:3219-3227.

Davidson, E.J. et al. 2003. "Human papillomavirus type 16 E2- and L1-specific serological and T-cell responses in women with vulval intraepithelial neoplasia." *J. Gen. Virol.* 84:2089-2097.

Davis, H.L. et al. "Direct gene transfer in skeletal muscle: Plasmid DNA based immunization against the hepatitis B virus surface antigen", *Vaccine*, vol. 12, No. 16, pp. 1503-1509 (1994).

De Jong, A. et al. 2002 "Frequent detection of human papillomavirus 16 E2-specific T-helper immunity in healthy subjects." *Cancer Res.* 62:472-479.

Desaintes, C. et al. 1997. "Expression of the papillomavirus E2 protein in HeLa cells leads to apoptosis." *EMBO J.* 16:504-514.

Dreicer, R. et al. 2005. "Phase II trial of GM-CSF + thalidomide in patients with androgen-independent metastatic prostate cancer." *Urol. Oncol.* 23:82-86.

Dorr, R.T. "Clinical properties of yeast—derived versus *Escheriichia coli*—deroved granulocyte—Macrophage Colony—stimulating factor", *Clin. Ther.*, vol. 15, pp. 19-29 (1993).

Eiben, G.L. et al. 2002. "Establishment of an HLA-A*0201 human papillomavirus type 16 tumor model to determine the efficacy of vaccination strategies in HLA-A*0201 transgenic mice." *Cancer Res.* vol. 62, pp. 5792-5799.

Eiben, G.L. et al. 2003 "Cervical cancer vaccines: recent advances in HPV research." *Viral Immunol.* 16:111-121.

Evans et al. "Rapid expression of an anti-human C5 chimeric Fab utilizing a vector that replicates in COS and 293 cells", *J. Immunol. Meth.*, vol. 184, pp. 123-138 (1995).

Feltkamp, "Vaccination with cytotoxic T lymphocyte epitope—containing peptide protects against a tumor induced by human papillomavirus type 16-transformed cells", *Eur. J. Immunol.*, vol. 23, pp. 2242-2249 (1993).

Fernando, G.J.P. et al. 1999. "Expression, purification and immunological characterization of the transforming protein E7, from cervical cancer-associated human papillomavirus type 16." *Clin. Exp. Immunol.* 115:397-403.

Frazer, I. 2002. "Vaccines for papillomavirus infection." *Virus Res.* 89:271-274.

Frazer, I.H. 2004. "Prevention of cervical cancer through papillomavirus vaccination." *Nat. Rev. Immunol.* 4:46-54.

Garrison, "Iontophoresis : An alternative drug—delivery system", *J. Med. Device Technol.*, vol. 9, pp. 32-36 (1998).

Genaro, A.O. "*Remington: the Science and Practice of Pharmacy*," Lippincott Williams & Wilkins (2005).

Gramzinski, R. et al. "Immune response to a hepatitis B DNA vaccine in Aotus Monkeys: A Comparison of vaccine formulation, route, and method of administration", *Mol. Med.*, vol. 4, pp. 109-118 (1998).

Greenstone, H.L. et al. 1998. "Chimeric papillomavirus virus-like particles elicit antitumor immunity against the E7 oncoprotein in an HPV16 tumor model." *PNAS USA* 95:1800-1805.

Gurunathan, S. et al. 1998. "CD40 ligand/trimer DNA enhances both humoral and cellular immune responses and induces protective immunity to infectious and tumor challenge." *J. Immunol.* 161:4563-4571.

Han, R. et al. 2000. "DNA vaccination prevents and/or delays carcinoma development of papillomavirus-induced skin papillomas on rabbits." *J. Virol.* 74:9712-9716.

Han, R. et al. 2000. "Immunization of rabbits with cottontail rabbit papillomavirus E1 and E2 genes: protective immunity induced by gene gun-mediated intracutaneous delivery but not by intramuscular injection." *Vaccine* 18:2937-2944.

Haj-Ahmad et al. "Development of a Helper- independent Human Adenovirus vector and its use in the transfer of the Herpes Simplex virus Thymidine Kindase Gene", *J. Virol.*, vol. 57, pp. 267-274 (1986).

Hegde, R.S. 2002. "The papillomavirus E2 proteins: structure, function and biology." *Annu. Rev. Biophys. Biomol. Struct.* 31:343-360.

Heiser, W.C. "Optimizing Electroporation conditions for the transformation of mammalian cells", *Methods Mol. Biol.*, vol. 130, pp. 117-134(2000).

Hogaard et al. "Comparative pharmacokinetics of single-dose administration of mammalian and bacterially derived recombinant human granulocyte-macrophage colony-stimulating factor", *Eur. J. Hematol.*, vol. 50, pp. 32-36 (1993).

Howard, J.P. et al. "Effects of Alternating Current Iontophoresis on Drug Delivery", *Arch. Phys. Med. Rehabil.*, vol. 76, pp. 463-466 (1995).

International Preliminary Report on Patentability dated Oct. 16, 2007 in corresponding PCT Application No. PCT/US2006/013315.

Kassan, D.G. et al. "Physical Enhancement of Dermatologic Drug Delivery: Iontophoresis and Phonophoresis", *J. Amer. Acad. Dermatol.*, vol. 34, pp. 657-666 (1996).

Kirnbauer et al. "Efficient Self-Assembly of Human Papillomavirus Type 16 L1 and L1-L2 into virus-like Particles", *J. Virol.*, vol. 67, pp. 6929-6936 (1993).

Kohler et al. "Continuous Cultures of Fused Cells Secreting Antibody of Predefined Specificity", *Nature*, vol. 256, pp. 495-497(1975).

Konya, J. et al. 1997. "Identification of a cytotoxic T-lymphocyte epitope in the human papillomavirus type 16 E2 protein." *J. Gen. Virol.* 78:2615-2620.

Kotin, "Prospects or the use of Adeno- Associated Virus as a Vector for Human Gene Therapy", *Human Gene Ther.*, vol. 5, pp. 793-801 (1994).

Koutsky, L.A. et al. 2002. "A controlled trial of a human papillomavirus type 16 vaccine." *N. Engl. J. Med.* 347:1645-1651.

Lebkowski et al. "Adeno-Associated Virus: A Vector System for Efficient Introduction and Integration of DNA into a Variety of Mammalian Cell Types", *Molec. Cell. Biol.*, vol. 8, pp. 3988-3996 (1988).

Lenz, P. et al. 2001. "Papillomavirus-like particles induce acute activation of dendritic cells." *J. Immunol.* 166:5346-5355.

Lenz, P. et al. 2003. "Interaction of papillomavirus virus-like particles with human myeloid antigen-presenting cells." *Clin. Immunol.* 106:231-237.

Lieschke et al. "Granulocyte Colony-Stimulating Factor and Granulocyte-Macrophage Colony-Stimulating Factor", *N. Engl. J. Med.*, vol. 327, pp. 28-35 (1992).

Lindmayer, I. et al. "Development of New Jet Injector for Insulin Therapy", *Diabetes Care*, vol. 9, No. 3, pp. 294-297, AdvantaJet, (1986).

Liu, X.S. et al. 2003. "IL-10 mediates suppression of the CD8 T cell IFN-response to a novel viral epitope in a primed host." *J. Immunol.* 171:4765-4772.

Lovvy, D.R. et al. 2003. "Chapter 16: prophylactic human papillomavirus vaccines." *J. Natl. Cancer Inst. Monogr.* 31:111-116.

Martins, J.K. et al. "A New Method of Corticosteroid-Anesthetic Delivery", *J. Occup. Med.*, vol. 21, pp. 821-824 (1979).

Miller et al. "Improved Retroviral Vectors for Gene Transfer and Expression", *BioTechniques*, vol. 7, pp. 980-990 (1989).

Miller, "Retrovirus Packaging Cells", *Human Gene Ther.*, vol. 1, pp. 5-14 (1990).

Mittereder et al. "Evaluation of the Efficacy and Safety of in Vivo, Adenovirus-Mediated Transfer of the Human Cystic Fibrosis Transmembrane Conductance Regulator cDNA",*Human Gene Ther.*, vol. 5, pp. 717-729, (1994).

Moniz, M. et al. 2003. "HPV DNA vaccines." *Front. Biosci.* 8:d55-68.

Moore, R.A. et al. 2003. "Therapeutic immunisation with COPV early genes by epithelial DNA delivery." *Virology* 314:630-635.

Muramatsu, T. et al. "In Vivo Electroporation: A Powerful and Convenient means of nonviral gene transfer to tissues of living animals", *Int. J. Mol. Med.*, vol. 1, pp. 55-62 (1998).

Muzyczka, N. "Use of Adeno-Associcated Virus as a General Transduction Vector for Mammalian Cells", *Current Topics Microbiol. Immunol.*, vol. 158, pp. 97-129 (1992).

Neumann E. et al. "Fundamentals of Electroporative Delivery of Drugs and Genes", *Bioelectrochem. Bioenerg.*, vol. 48, pp. 3-16 (1999).

Newberg, M.H. et al. 1996. "Importance of MHC class 1, α 2 and α 3 domains in the recognition of self and non-self MHC molecules." *J. Immunol.* 156:2473-2480.

Oh, Y.-K. et al. 2004. "Enhanced mucosal and systemic immunogenicity of human papillomavirus-like particles encapsidating interleukin-2 gene adjuvant." *Virology*, 328:266-273.

Ottaiano, A. et al. 2002. "CD40 activation as potential tool in malignant neoplasms." *Tumori* 88:361-366.

Parkin et al., "Global Cancer Statistics", *CA Cancer J. Clin.*, vol. 49, pp. 33-64 (1999).

Pastrana, D.V. et al. 2001. "NHPV16 VLP vaccine induces human antibodies that neutralize divergent variants of HPV16." *Virology* 279:361-369.

Pisani et al. "Estimates of the Worldwide Mortality from 25 Cancers in 1990", *Int J. Cancer*, vol. 83, pp. 18-29 (1999).

Prakash, S.S. et al. 1992. "Amino acids necessary for DNA contact and dimerization imply novel motifs in the papillomavirus E2 transactivator." *Genes Dev.* 6:105-116.

Pulito et al. "Humanization and Molecular Modeling of the Anti-CD4 Monoclonal Antibody, OKT4A", *J. Immunol.*, vol. 156, pp. 2840-2850 (1996).

Qian, J. et al. 2006. "Combined prophylactic and therapeutic cancer vaccine: enhancing CTL responses to HPV16 E2 using a chimeric VLP in HLA-A2 mice." *Int. J. Cancer* 118:3022-3029.

Qin, J.Y. et al. "Gene Suture—A Novel Method for Intramuscular Gene Transfer and its Application in Hypertension Therapy", *Life Sciences*, vol. 65, pp. 2193-2203 (1999).

Ressing, M.E. et al. 1995. "Human CTL epitopes encoded by human papillomavirus type 16 E6 and E7 identified through in vivo and in vitro immunogenicity studies of HLA-A*0201-binding peptides." *J. Immunol.* 154:5934-5943.

Rich et al. "Development and Analysis of Recombinant Adenoviruses for Gene Therapy of Cystic Fibrosis", *Human Gene Ther.*, vol. 4, pp. 461-476 (1993).

Ridge et al. "A Conditioned Dendritic Cell can be a Temporal Bridge Between a CD4+ T-helper and a T-killer Cell", *Nature*, vol. 393, pp. 474-478(1998).

Riechmann et al. "Reshaping Human Antibodies for Therapy", *Nature*, vol. 332, pp. 323-327 (1988).

Riviere et al. "Electrically—Assisted Transdermal Drug Delivery", *Pharm. Res.*, vol. 14, pp. 687-697 (1997).

Rolink, A. et al. "The SCID but not the RAG-2 Gene Product is required for Su-Se Heavy Chain Class Switching" *Immunity*, vol. 5, pp. 319-330 (1996).

Rosales, C. et al. 2000. "A recombinant vaccinia virus containing the papilloma E2 protein promotes tumor regression by stimulating macrophage antibody-dependent cytotoxicity." *Cancer Immunol. Immunother.* 49:347-360.

Schafer, K. et al. 1999. "Immune response to human papillomavirus 16 L1E7 chimeric virus-like particles: induction of cytotoxic T cells and specific tumor protection." *Int. J. Cancer* 81:881-888.

Schiller, J.T. et al. 2001. "Papillomavirus-like particle based vaccines: cervical cancer and beyond." *Expert Opin. Biol. Ther.* 1:571-581.

Schiller, J.T. et al. 2004. "Delivering on the promise: HPV vaccines and cervical cancer." *Nat. Rev. Microbiol.* 2:343-347.

Schrijver, R.S. et al. "Immunization of Cattle with a BHVI Vector Vaccine or a DNA Vaccine Both Coding for the G Protein of BRSV", *Vaccine*, vol. 15, pp. 1908-1916 (1997) Pigjet.

Selvakumar, R. et al. 1995. "Tumor regression is associated with a specific immune response to the E2 protein of cottontail rabbit papillomavirus." *Virology* 208:298-302.

Shi, W. et al. 1999. "Human papillomavirus type 16 E7 DNA vaccine: mutation in the open reading frame of E7 enhances specific cytotoxic T-lymphocyte induction and antitumor activity." *J. Virol.* 73:7877-7881.

Singh and Maibach, "Topical Iontophoretic Drug Delivery in Vivo: Hisorical Development devices and Future Prespectives", *Dermatology*, vol. 187, pp. 235-238 (1993).

Singh, J. et al. "Transdermal Delivery of Drugs by Iontophoresis: A Review", *Drug Des. Deliv.*, vol. 4, pp. 1-12 (1989).

Singh, P. et al. "Iontophoresis in Drug Delivery: Basic Principles and Applications", *Crit. Rev. Ther. Drug Carrier Syst.*, vol. 11, pp. 161-213 (1994).

Stanley, M.A. 2003. "Progress in prophylactic and therapeutic vaccines for human papillomavirus infection." *Expert Rev. Vaccines* 2:381-389.

Stevenson, M. et al. 2000. "Inverse relationship between the expression of the human papillomavirus type 16 transcription factor E2 and virus DNA copy number during the progression of cervical intraepithelial neoplasia." *J. Gen. Virol.* 81:1825-1832.

Storni, T. et al. 2002. "Critical role for activation of antigen-presenting cells in priming of cytotoxic T cell responses after vaccination with virus-like particles." *J. Immunol.* 168:2880-2886.

Su, Y. et al. "Quantitative in Vivo Iontophoretic Studies", *J. Pharm. Sci.*, vol. 83, pp. 12-17 (1994).

Technical Product Report: LEUKINE Liquid, Immunex Corp., Seattle, Wash., 1997.

Theiss, U. et al. "Iontophoresis—Is there a Future for Clinical Application?", *Methods Find. Exp. Clin. Pharmacol.*, vol. 13, pp. 353-359 (1991).

Vahlsing, H. et al. "Immunization with Plasmid DNA Using a Pneumatic Gun", *J. Immunol. Methods*, vol. 175, pp. 11-22 (1994).

Velders, M.P. et al. 2001. "Eradication of established tumors by vaccination with Venezuelan equine encephalitis virus replicon particles delivering human papillomavirus 16 E7 RNA." *Cancer Res.* 61:7861-7867.

Villa, et al. 2005. "Prophylactic quadrivalent human papillomavirus (types 6, 11, 16 and 18) L1 virus-like particle vaccine in young women: a randomised double-blind placebo-controlled multicentre phase II efficacy trial." *Lancet Oncol.* 6:271-278.

Vincent et al. "Replication and packaging of HIV Envelope Genes in a Novel Adeno-Associated Virus Vector System", *Vaccines 90* (Cold Spring Harbor Laboratory Press) (1990).

*New Trends and Developments in Vaccines*, Voller et al. (eds.), University Park Press, Baltimore, Md. (1978).

Xu et al. "Residue at position 331 in the IgG1 and IgG4 Ch2 Domains Contributes to their Differential Ability to Bind and Activate Complement", *J. Biol. Chem.*, vol. 269, pp. 3469-3474 (1994).

Zempsky, W.T. et al., "Iontophoresis: Noninvasive Drug Delivery", *Amer. J. Anesthesiol.*, vol. 25, pp. 158-162 (1998).

Zwaveling, et al. 2002. "Established human papillomavirus type 16-expressing tumors are effectively eradicated following vaccination with long peptides." *J. Immunol.* 169:350-358.

* cited by examiner

Figure 3
Panel A
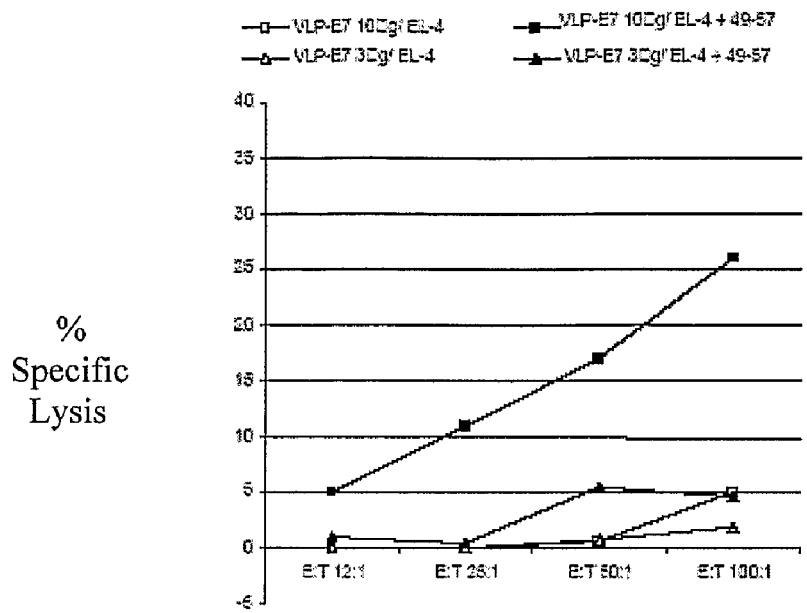
Panel B
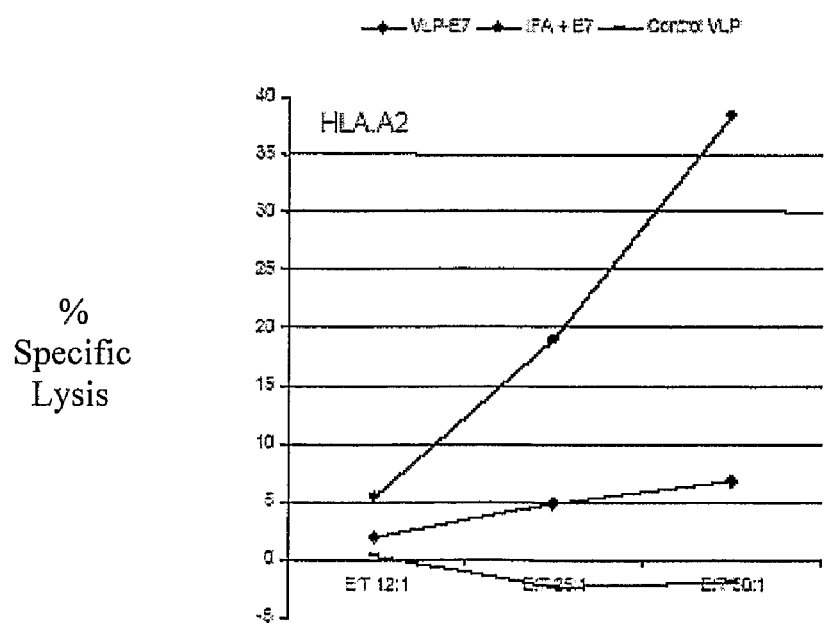

Figure 8
Panel A
Ex-vitro ELISPOT
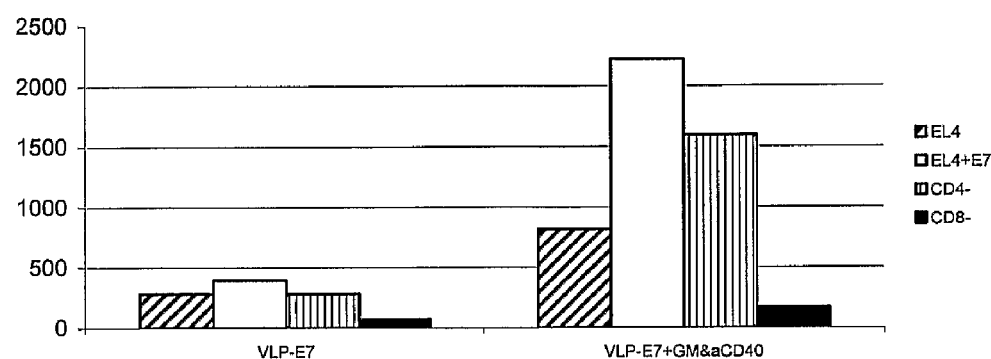
Immunization
Panel B
CTL assay
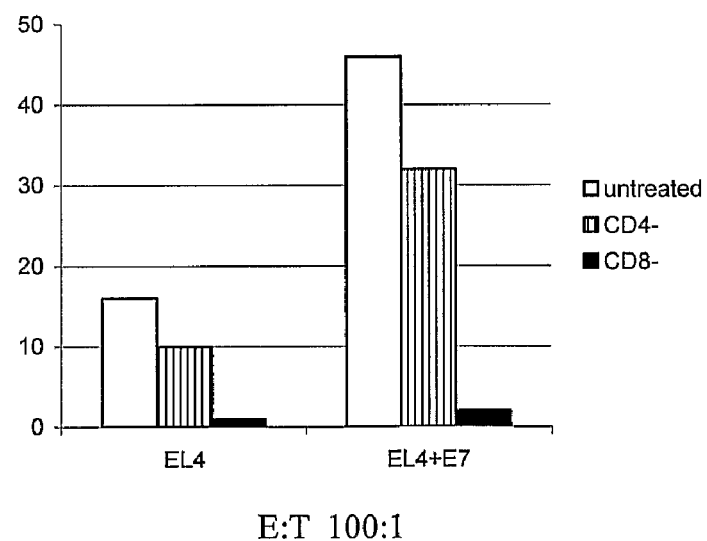
E:T 100:1

Figure 10
Panel A
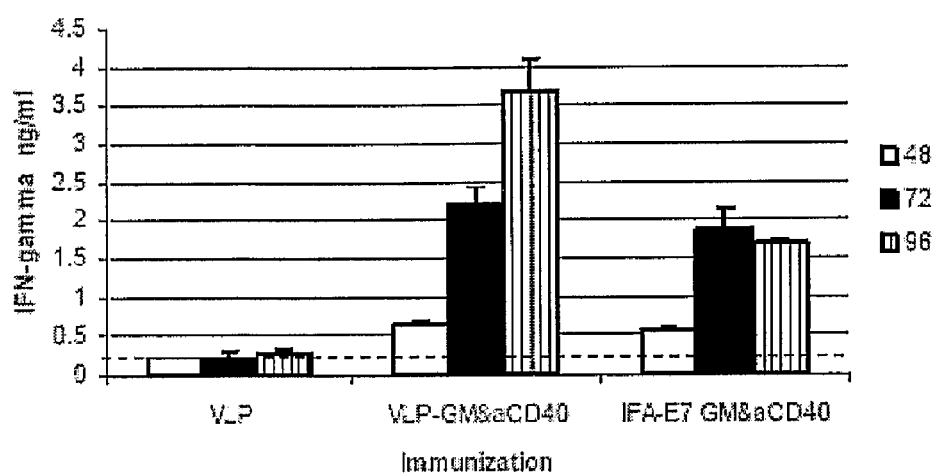
Panel B
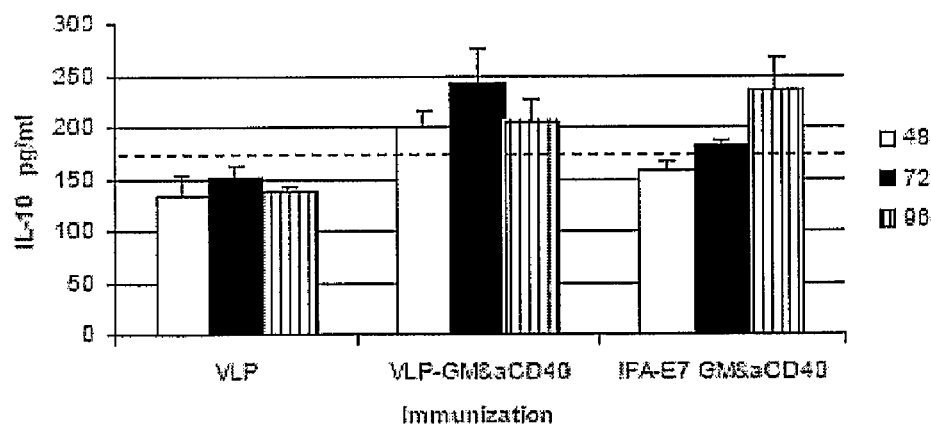

Figure 11
Panel A
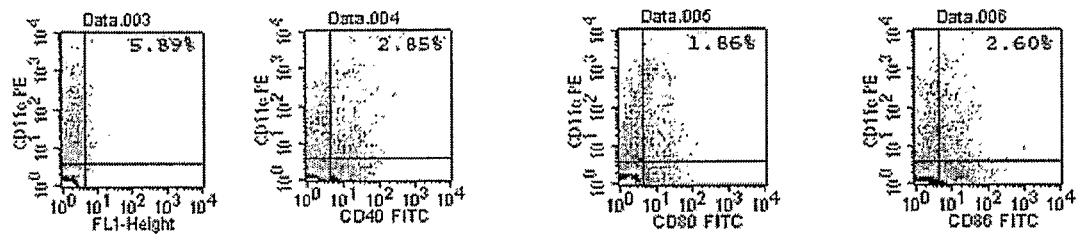
Panel B
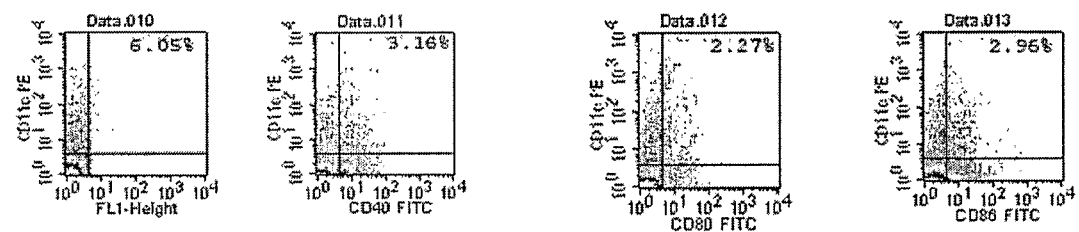
Panel C
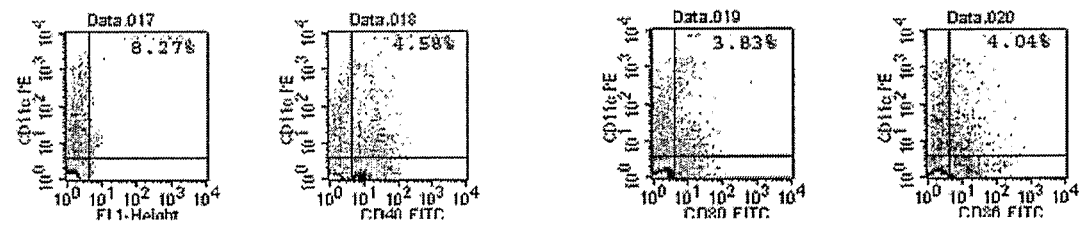
Panel D
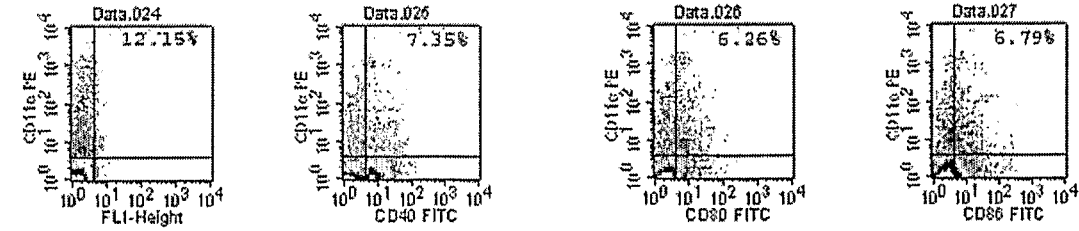

Figure 19
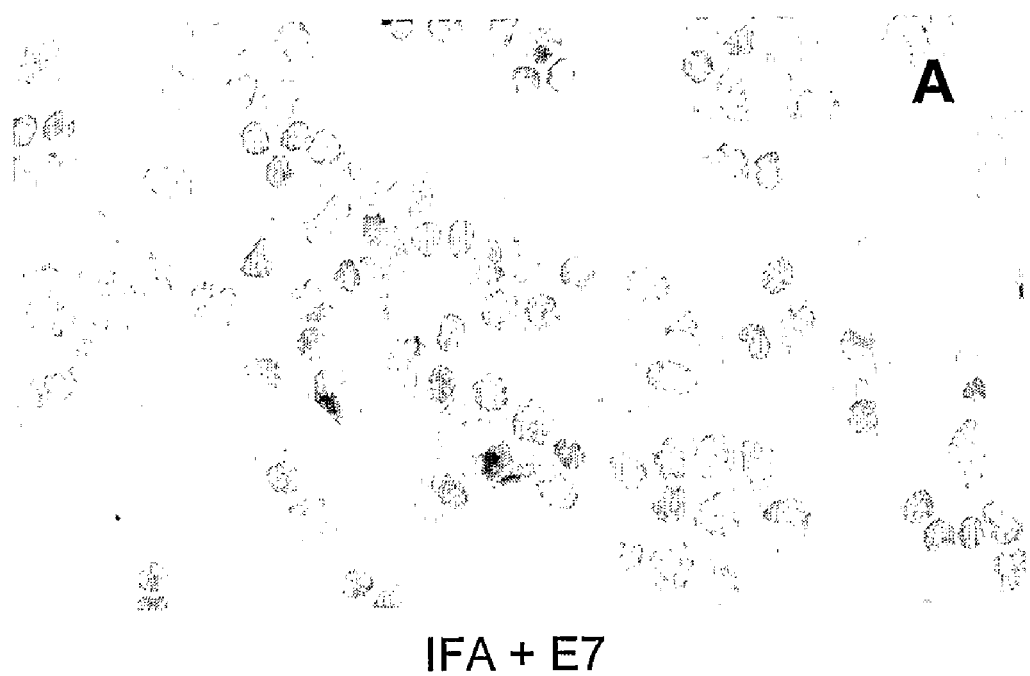
IFA + E7
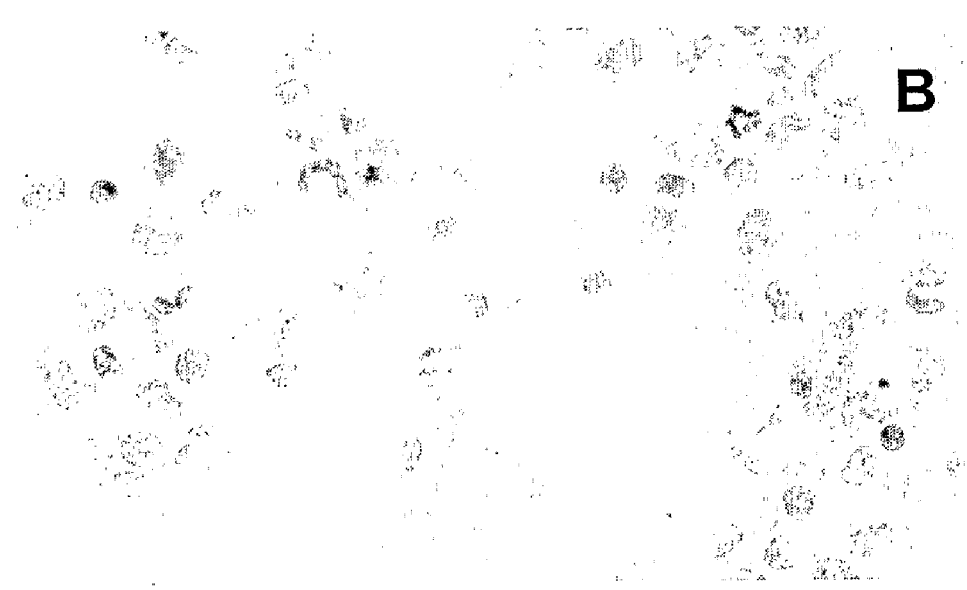
IFA + E7 + aCD40

Figure 20

HLA.A2 Binding Assay

E2   138-147      YICEeASVTV
E2   Modified     YLAEeASVTV

METHODS AND COMPOSITIONS FOR PRODUCING AN ENHANCED IMMUNE RESPONSE TO A HUMAN PAPILLOMAVIRUS IMMUNOGEN

CROSS-REFERENCE TO RELATED APPLICATIONS

This application is a U.S. National Phase of International Application No. PCT/US2006/013315, filed Apr. 11, 2006, designating the U.S. and published in English as WO 2006/113209 on Oct. 26, 2006, which claims the benefit of U.S. Provisional application No. 60/671,463, filed Apr. 15, 2005; U.S. Provisional application No. 60/680,000, filed May 12, 2005; and U.S. Provisional application No. 60/724,783, filed Oct. 11, 2005, all of which are hereby expressly incorporated by reference in their entireties.

BACKGROUND OF THE INVENTION

1. Field of the Invention

The present invention relates to novel methods for producing an enhanced immune response to persistent infections by the human papillomavirus.

2. Description of the Related Art

Human papillomavirus (HPV) infections are associated with a spectrum of epithelial diseases from benign warts to cervical intraepithelial neoplasia (CIN) to invasive carcinoma. Additionally, HPV infection is found in more than half of the patients with colorectal cancer (Bodaghi et al. 2005 *Clin. Cancer Res.* 11:2862-2867). Almost all cervical cancer is caused by HPV infection, most often HPV16 (Frazer, 2004 *Nat. Rev. Immunol.* 4:46-54). In developing countries, cervical cancer is often the most frequent female malignancy and constitutes up to a quarter of all female cancers (Pisani et al. 1999 *Int. J. Cancer* 83:18-29; Parkin 1999 *CA Cancer J. Clin.* 49:33-64). In light of these facts, the development of effective HPV vaccines could contribute greatly to the prevention and treatment of cervical cancer. Substantial advances have been made in developing HPV prophylactic vaccines based on L1 virus-like particles (VLPs) that induce neutralization antibody to L1 (Villa, L. L. et al. 2005 *Lancet Oncol.* 6:271-278; Schiller, J. T. et al. 2001 *Expert Opin. Biol. Ther.* 1:571-581; Lowy, D. R. et al. 2003 *J. Natl. Cancer Inst. Monogr.* 111-116; Koutsky, L. A. et al. 2002 *N. Engl. J. Med.* 347:1645-1651). It has been shown that HPV 16 VLPs can generate high titers of virus-neutralizing antibodies, and they have been 100% effective at preventing persistent HPV 16 infection in clinical trials (Frazer 2004 *Nat. Rev. Immunol.* 4:46-54). By contrast, therapeutic HPV vaccines have not yet demonstrated high efficacy against cervical cancer or premalignant HPV-induced neoplasia in clinical trials (Stanley 2003 *Expert Rev. Vaccines* 2:381-389). An effective combined prophylactic/therapeutic vaccine would be especially attractive for cervical cancer prevention. It could promote mass immunization programs of both preadolescent and older women, many of whom have already been exposed to genital tract HPV infection, and thereby promote more rapid development of effective immunity. A combined vaccine could offer the best combination of immediate impact and long term effectiveness. It will be particularly useful in developing countries, where most women with prevalent infection do not have access to quality Pap screen programs to reduce their risk of cervical cancer (Schiller, J. T. et al. 2004 *Nat. Rev. Microbiol.* 2:343-347).

HPV E6 and E7 are constitutively expressed in cervical cancer cells, and therefore provide attractive targets for a therapeutic vaccine. Therapeutic vaccine strategies targeting E6 and E7 have included peptides (Ressing et al. 1995 *J. Immunol.* 154:5934-5943), recombinant E6 and E7 proteins (Fernando et al. 1999 *Clin. Exp. Immunol.* 115:397-403), viral vectors (Velders et al. 2001 *Cancer Res.* 61:7861-7867), and plasmid DNA (Eiben et al. 2002 *Cancer Res.* 62:5792-5799; Shi et al. 1999 *J. Virol.* 73:7877-7881).

During the HPV infection, the HPV16 E2 gene is likely uniformly expressed during the productive viral infection in CIN1 and CIN2 (Hegde, R. S. 2002 *Annu. Rev. Biophys. Biomol. Struct.* 31:343-360). HPV 16 E6 and E7 genes are expressed in CIN2, CIN3 and cervical cancer cells, and have been the main focus of HPV therapeutic vaccines.

The E2 gene is highly expressed in low grade CIN, and lost when the lesion progresses to invasive carcinoma (Stevenson, M. et al. 2000 *J. Gen. Virol.* 81:1825-1832). In a cottontail rabbit papillomavirus (CRPV) model, immune response against E2 is associated with spontaneous regression of papillomas (Selvakumar, R. et al. 1995 *Virology* 208:298-302). Therefore, E2 and E7 provide attractive targets for a therapeutic vaccine with treatment ranging from low-grade diseases, such as CIN, VIN, and AIN, to malignant carcinoma (Rosales, C. et al. 2000 *Cancer Immunol Immunother.* 49:347-360; Eiben, G. L. et al. 2003 *Viral Immunol.* 16:111-121). Vaccine strategies targeting E6 and E7, using peptides (Ressing, M. E. et al. 1995 *J. Immunol.* 154:5934-5943), proteins (Fernando, G. J. et al. 1999 *Clin. Exp. Immunol.* 115:397-403), viral vectors (Velders, M. P. et al. 2001 Cancer Res. 61:7861-7867) and plasmid DNA (Shi, W. et al. 1999 *J. Virol.* 73:7877-7881; Moniz, M. et al. 2003 *Front. Biosci.* 8:d55-68), have been reported. However, there is only limited information on the CD8+ T cell response to E2 (Rosales, C. et al. 2000 *Cancer Immunol. Immunother.* 49:347-360; de Jong, A. et al. 2002 *Cancer Res.* 62:472-479). Therefore, development of a vaccine targeting E2 would be useful in the treatment of low-grade diseases caused by HPV infection, such as CIN, VIN, and AIN, and in the prevention of the subsequent development of HPV-associated anogenital cancers.

Experimental evaluation of therapeutic HPV vaccine strategies has involved C57BL/6 mice and H-2K$^b$ restricted T cell epitopes (Feltkamp 1993 *Eur. J. Immunol.* 23:2242-2249). These studies have provided limited predictive value regarding HLA-restricted responses in humans. However, HLA-A2 transgenic mice have been used to evaluate the presentation of chimeric VLP epitopes by a human MHC-1 molecule. It has been shown that CD8$^+$ T cells from HLA-A2 mice recognize the same HLA-A2-restricted peptides as are recognized by human T cells (Ressing et al. 1995 *J. Immunol.* 154:5934-5943; Eiben et al. 2002 *Cancer Res.* 62:5792-5799). These studies indicate the efficacy of using HLA-A2 transgenic mice to evaluate the strategies for vaccine development.

In mice, chimeric VLPs have been shown to induce HPV16-neutralizing antibodies and immune responses against challenge by synergistic tumor cells expressing E7 (Frazer 2002 *Virus Res.* 89:271-274; Pastrana 2001 *Virology* 279:361-369). In addition, chimeric VLPs were able to induce T cell responses, in the absence of a conventional adjuvant, such as Incomplete Freund's Adjuvant (IFA). VLPs are bound and internalized by monocytes, macrophages and myeloid dendritic cells (DCs) in vitro (Storni et al. 2002 *J. Immunol.* 168:2880-2886; Da Silva 2001 *Int. Immunol.* 13:633-641).

Therefore, the development of optimized immunization strategies for use in combination with HPV VLP and other HPV immunogens is a critical need. The invention described herein is directed to address this and other needs.

SUMMARY OF THE INVENTION

In detail, the invention concerns a method of treating a persistent human papillomavirus infection in a subject comprising administering to the subject
- (a) a prime immunization comprising an HPV virus like particle comprising a first HPV E2 polypeptide; and
- (b) at least one boost immunization comprising a second HPV E2 polypeptide having a CTL epitope;
- wherein a CD40 agonist and a GM-CSF agent are administered in conjunction with at least one of the prime immunization or the boost immunization.

The invention further concerns a method of treating a persistent human papillomavirus infection in a subject comprising administering to the subject
- (a) a prime immunization comprising a first E2 polypeptide having a CTL epitope; and
- (b) at least one boost immunization comprising an HPV virus like particle comprising a second E2 polypeptide having a CTL epitope;
- wherein a CD40 agonist and a GM-CSF agent are administered in conjunction with one of the prime immunization or the boost immunization.

The invention further concerns the embodiment of any of such methods wherein the CTL epitope is selected from the group consisting of:
- E2 138-147 (YICEEASVTV) (SEQ ID NO: 1);
- E2 69-77 (ALQAIELQL) (SEQ ID NO: 2); and
- E2 138-147 modified (YLAEEASVTV) (SEQ ID NO: 9).

The invention further concerns the embodiments of any of such methods wherein a memory CTL response of greater than five years is obtained.

The invention further concerns the embodiments of any of such methods wherein the subject is a human subject (especially a human subject having a condition selected from the group consisting of CIN, VAIN, VIN, or AIN).

The invention further concerns the embodiments of any of such methods wherein the second HPV E2 polypeptide comprises HLA-A2 binding activity.

The invention further concerns the embodiments of any of such methods wherein the CD40 agonist is an anti-CD40 antibody, or fragment thereof.

The invention further concerns the embodiments of any of such methods wherein the HVP virus like particle further comprises an E7 polypeptide.

The invention further concerns the embodiments of any of such methods wherein the first E2 polypeptide is contained on the same polypeptide chain as the HVP L2 protein.

The invention further concerns a method of treating a persistent human papillomavirus infection in a subject comprising administering to the subject an immunization comprising an E2 polypeptide comprising a CTL epitope selected from the group consisting of:
- E2 138-147 (YICEEASVTV) (SEQ ID NO: 1);
- E2 69-77 (ALQAIELQL) (SEQ ID NO: 2); and
- E2 138-147 modified (YLAEEASVTV) (SEQ ID NO: 9).
- wherein the polypeptide is administered to the subject in conjunction with a CD40 agonist and a GM-CSF agent.

The invention further concerns the embodiment of any of the above described methods, further comprising the step of administering to the subject a boost immunization comprising an E2 polypeptide comprising a CTL epitope.

BRIEF DESCRIPTION OF THE DRAWINGS

FIG. 3 shows the results of an analysis of T cell response from immunized C57B1V6 mice and HLA.A2 transgenic mice. Mice are immunized with the L1-VLP-L2-E7-E2 construct, a control L1-VLP-L2 construct, or E7 peptides with GM-CSF and IL-2 in an IFA emulsion. Spleen cells are taken two weeks after immunization and re-stimulated with E7 peptides for seven days in vitro prior to a cytolytic T-lymphocyte (CTL) analysis. Panel A shows the results obtained using spleen cells from C57BL/6 mice, wherein EL-4 target cells are pulsed with or without E7 49-57 peptides. Panel B shows the results obtained using spleen cells from HLA.A2 transgenic mice, wherein C1R.ADD target cells are pulsed with E7 11-20 and 86-93 peptides. The lysis of target cells alone is less then 2%. Data are expressed as an average of triplicate wells with an SD of less then 15%.

FIG. 8 shows an analysis of the role of CD8+ T-cells in the L1-VLP-L2-E2-E7 induced T cell response. Mice are immunized with L1-VLP-L2-E2-E7 alone or with L1-VLP-L2-E2-E7 in combination with GM-CSF and an anti-CD40 antibody. Spleen cells are taken two weeks after immunization and re-stimulated for 7 days in vitro with E7 49-57 peptides. CD4 and CD8 positive cells are depleted by magnetic beads at day 7. The results of an ELIOSPOT assay are shown in Panel A, and the results of a CTL assay are shown in Panel B. Target cells are EL-4 cells pulsed with or without E7 peptides. The CTL assay is conducted at an effector cell/target cell ratio (E:T) of 100:1. Data are expressed as an average from triplicate wells.

FIG. 10 shows the results of an ELISA analysis of cytokine production (IFN-gamma and IL-10) in spleens cells isolated from C57BL/6 mice immunized with the following preparations: (a) L1-VLP-L2-E7-E2+IFA, (b) L1-VLP-L2-E7-E2+GM-CSF+αCD40+IFA, or (c) E7 49-57+GM-CSF+αCD40+IFA. Spleens are taken two weeks after immunization and spleen cells are stimulated with E7 49-57 in vitro. The supernatant is collected at 48, 72 and 96 hours for ELISA assay, and the dashed lines in Panel A and Panel B indicated the average of ELISA readout of cells cultured with medium alone.

FIG. 11 shows a FACScan analysis of the recruitment and activation of dendritic cells (DCs) in HLA.A2 transgenic mice. The Figure shows the recruitment and activation DCs in AAD mice: Mice were immunized with VLP-E7E2 with or without GM and αCD40. Draining lymph nodes were collected six days after immunization for FACScan analysis. Mice are immunized with 10 µg of chimeric VLP-E7 with or without GM-CSF or an anti-CD40L antibody. Draining inguinal lymph nodes are collected one week after immunization for FACScan analysis. The immunization protocols employed are as follows: Panel A—VLP-E7; Panel B—VLP-E7F+GM-CSF; Panel C—VLP-E7+anti-CD40 antibody; Panel D—VLP-E7+GM-CSF+anti-CD40 antibody. For Data 003, 010, 017, and 024, the percentage of gated is the sum of the number from the upper left and upper right quadrants. For the rest of the data, the percentage of gated is the number from the upper right quadrant indicating the CD80, CD 86 and CD40 positive cells.

FIG. 19 shows the immunohistochemistry staining of IL-15 in CD11c+dendritic cells from immunized mice. Panel A shows cells from mice immunized with IFA+E7 49-57 peptides and Panel B shows cells immunized with IFA+E7 49-57 peptides+anti-CD40 antibody.

FIG. 20 shows that the modified E138-147 peptide (SEQ ID NO: 9) exhibited a higher HLA.A2 binding affinity than the unmodified (wild type) E138-147 peptide (SEQ ID NO: 1).

DETAILED DESCRIPTION OF THE PREFERRED EMBODIMENT

Figure 1:
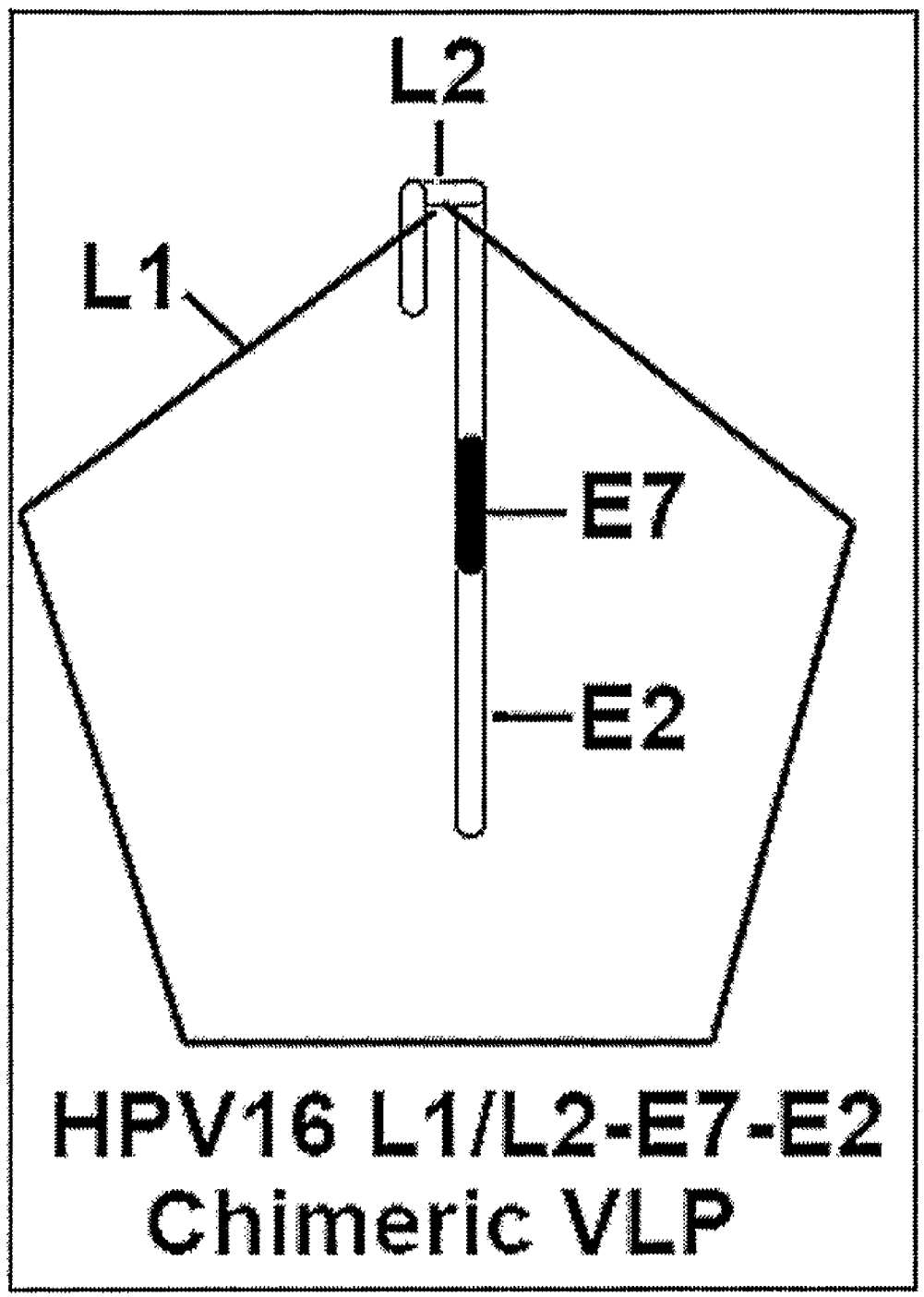
FIG. 1 shows a schematic diagram of the HPV16 L1/L2-E7-E2 chimeric virus-like particle (VLP) (L1-VLP-L2-E7-E2).

The invention relates, in part, to the recognition that the co-administration to a subject of a CD40 agonist and granulocyte/macrophage colony stimulating factor (GM-CSF) agent as adjuvants in conjunction with the administration of a human papillomavirus (HPV) immunogen provides unexpected benefits in enhancing the immune response to the immunogen.

The invention further relates to the recognition that CD40 agonists and GM-CSF agents act synergistically to enhance the immune response to HPV immunogens, particularly to the HPV E2 protein. In one aspect, CD40 agonists and GM-CSF agents act synergistically in conjunction with an immunogen, particularly an HPV E2 protein, to enhance the cytolytic T-cell response to cells expressing the immunogen. The invention also relates to the recognition that an immunization strategy that employs HPV virus like particles that comprise the E2 protein as one immunogen and HPV polypeptides comprising CTL epitopes as a second immunogen, in conjunction with GM-CSF and a CD40 agonist provides an optimal CTL response to E2 expressing cells.

Thus, the invention also relates to a therapeutic vaccine against persistent HPV infection, including HPV induced neoplasia and cancer. HPV induced neoplasias that may be treated or prevented with the methods of the invention include, for example, cervical intraepithelial neoplasia (CIN), vulval intraepithelial neoplasia (VIN), vaginal intraepithelial neoplasia (VAIN), and anal intraepithelial neoplasia. HPV associated cancers of, for example, the cervix, vulva, vagina, and anus may also be treated or prevented with the methods of the present invention.

As used herein, "HPV" and "human papillomavirus" refer to the members of the genus Papillomavirus that are capable of infecting humans. There are two major types of HPVs (i.e. genital and cutaneous groups), each of which contains multiple virus "types" or "strains" (e.g., HPV 16, HPV 18, HPV 31, HPV 32, etc. in the genital group). Of particular interest in the present invention are the HPV types that are most associated with genital infection and malignancy.

As used herein, the term "subject" refers to a warm-blooded vertebrate animal, preferably a mammal. Specific subjects may include domestic pets such as cats and dogs, guinea pigs, rabbits, etc., farm animals such as horses, cows, pig, sheep, goats, chickens, etc. A preferred subject is a human subject, especially a female human subject.

As used herein, the term "CTL epitope" or "cytolytic T cell epitope" refers to a feature of a molecule or protein that is recognized by a CD 8+T-cell receptor.

In one aspect the invention relates to the identification of cytolytic T cell epitopes (CTL epitopes) of HPV proteins and to methods of using such epitopes to generate a therapeutic CTL response against HPV infected cells. In preferred embodiments, the invention relates to E2 CTL epitopes, preferably to the following E2 CTL epitopes:

E2 138-147 (YICEEASVTV) (SEQ ID NO: 1);
E2 69-77 (ALQAIELQL) (SEQ ID NO: 2); and
E2 138-147 modified (YLAEEASVTV) (SEQ ID NO: 9).

and to polypeptides comprising these epitopes. Polypeptides comprising these epitopes preferably retain in vitro binding activity to HLA-A2 expressing cells.

In another aspect, the invention relates to the recognition that the co-administration of CD40 agonists and GM-CSF agents with an HPV immunogen acts to provide unexpected improvements in the memory cytolytic T-cell response to the HPV immunogen, particularly providing for a significant cytolytic T-cell response to the immunogen that persists in a subject for an extended period of time after the initial immunization of the subject. As used herein, the "initial immunization" refers to the immunization schedule employed to generate a significant cytolytic T-cell response. Thus, the initial immunization may comprise a single immunization or a prime and a boost immunization.

In preferred embodiments, a memory cytolytic T-cell response will persist for a time period of at least about 5%, 10%, 20%, 30%, 40% or 50% of the average life span for a particular organism. For example, in a human subject, a memory cytolytic T-cell response will persist for a time period of at least 2 years, preferably at least 5 years, more preferably at least 8 years, and most preferably at least 10 years.

In one aspect, the invention relates to the recognition that the co-administration of CD40 agonists and GM-CSF agents to a subject acts to increase IL-15 production by the subjects dendritic cells. Thus, the invention relates to the recognition that the co-administration of CD40 agonists and GM-CSF agents to a subject may useful in boosting the IL-15 production in a subject in need thereof, particularly subjects having cancer or infectious disease.

CD40 Agonist

The invention thus provides methods, compositions and uses of one or more CD40 agonists, such as CD40 ligands and/or agonistic anti-CD40 antibodies. All CD40 agonists are suitable for use in the invention, so long as they bind to and activate one or more CD40 receptors on a cell. A CD40 agonist that "binds to and activates" a CD40 receptor is a biological or chemical component or agent that stimulates cell signaling via CD40 in such cells. "Cell signaling" via a CD40 receptor is indicated by the capacity to "transduce" a signal, i.e., transmit a biological effect, to the intracellular environment by binding of an agent to an extracellular portion of the receptor. Most preferably, CD40 agonists bind to and activate a CD40 receptor on an antigen presenting cell, preferably a dendritic cell.

Agents that "stimulate" cell signaling via CD40 receptors may do so directly or indirectly. Although agents that act directly are generally preferred, agents that indirectly stimulate or activate CD40 receptors may be used, including accessory signaling molecules, co-stimulators and the like, and agents that remove, inactivate or downregulate inhibitors of the CD40 signaling process. Included within this group of CD40 agonists are agents that stimulate or "upregulate" the expression of the CD40 receptor on dendritic cells. Such components will therefore increase the amount of the receptor expressed at the cell surface and available for binding to the natural biological ligand counterpart or exogenously added CD40 ligands.

CD40 agonists that directly stimulate or activate CD40 receptors include the biological ligand counterparts to the receptor. As used herein, the term "CD40 ligand" will be understood to include any peptide, polypeptide or protein, or a nucleic acid encoding a peptide, polypeptide or protein that can bind to and activate one or more CD40 receptors on a cell. Suitable CD40 ligands are described, for example, in U.S. Pat. No. 6,482,411.

Although human CD40 ligands will be preferred for use in human therapy, CD40 ligands from any species may be used in the invention. For use in other animal species, such as in veterinary embodiments, a species of CD40 ligand matched to the animal being treated will be preferred.

A CD40 ligand "protein, polypeptide or peptide", as used herein, refers to a proteinaceous CD40 ligand component that has sufficient biological activity to be biologically effective. Accordingly, "CD40 ligands" include full-length CD40 ligand proteins and polypeptides and also CD40 ligands that have been subject to non-native processing or biological modification. Such modifications include truncations, extensions, active domains or fragments, fusion proteins, mutants with substantial or sufficient biological activity, peptidomimetics and the like.

Any form of CD40 ligand may be used in the invention, including those isolated and purified from natural sources. CD40 ligands prepared by recombinant expression will often be preferred, i.e., those obtained by expressing a CD40 ligand nucleic acid in a recombinant host cell and collecting the expressed CD40 ligand protein. CD40 ligands prepared by automated peptide synthesis are also contemplated.

In certain embodiments, the CD40 ligand is a soluble gp39 peptide, polypeptide or protein, or at least a first nucleic acid encoding a soluble gp39 peptide, polypeptide or protein. CD40 ligands are described, for example, in U.S. Patent Publication No. 20030099644, herein incorporated by reference. In preferred embodiments, the at least a first CD40 ligand is at least a first soluble gp39 protein that comprises all, substantially all or most of the extracellular domain. In particular aspects, the extracellular domain of the gp39 protein comprises the human sequence from between about amino acid 47-50 to about amino acid 261. Sequences of from between about amino acid 47-50 to about amino acid 260 of the corresponding murine, canine, feline or rat sequences may be used, as disclosed in U.S. Patent Publication No. 20030099644, incorporated herein by reference. As used herein, the term "between about amino acid 47-50 to about amino acid 260 or 261" will be understood to include sequences between amino acid 45, 46, 48, 49, 51 and 52 or so to about amino acid 257, 258, 259, 260 and 261 or so.

"CD40 ligand nucleic acids" are DNA or RNA coding regions that encode, and under conditions appropriate for expression, encode and express any one or more of the biologically active CD40 ligand protein- and polypeptide-based components described above, including full-length proteins and polypeptides, and active variants, fragments and fusions thereof. Recombinant vectors, viral vectors and recombinant viruses are preferred for use in various embodiments, as described in detail herein.

Particularly preferred embodiments of the invention are those wherein the at least a first CD40 ligand is a gp39 peptide or protein oligomer, including naturally forming gp39 peptide, polypeptide or protein oligomers, as well as gp39 peptides, polypeptides, proteins (and encoding nucleic acids) that comprise an oligomerization sequence. While oligomers such as dimers, trimers and tetramers are preferred in certain aspects of the invention, in other aspects of the invention larger oligomeric structures are contemplated for use, so long as the oligomeric structure retains the ability to bind to and activate one or more CD40 receptor(s).

Other preferred embodiments are those wherein the CD40 agonist is a component other than one based upon the natural, biological ligand. As used herein, the term "CD40 agonist" thus includes proteins, polypeptides, peptides, antibodies, small molecules and other agents that bind to and activate a CD40 receptor. Thus, CD40 "agonists" are operationally similar to CD40 "ligands", although the agonists are not limited to derivatives of CD40 ligands, but rather include all operative species irrespective of the underlying molecular structure.

In certain preferred aspects, the "CD40 agonist" is an anti-CD40 antibody, or antigen-binding fragment thereof, including, but not limited to, a scFv, Fv, Fab', Fab or F(ab')$_2$ antigen-binding region of an anti-CD40 antibody. In certain aspects of the invention, the CD40 agonist is a human, humanized or part-human chimeric anti-CD40 antibody or antigen-binding fragment thereof. In other aspects, the CD40 agonist is an anti-CD40 monoclonal antibody, including, but not limited to, the G28-5, mAb89, EA-5 or S2C6 monoclonal antibody, or an antigen-binding fragment thereof.

The CD40 binding molecules of the invention can be made by conventional production and screening techniques. A rat and a hamster anti-mouse CD40 monoclonal antibody ("Mabs") are each described in Ridge et al. (1998 *Nature* 393:474-77) and are available commercially (Pharmingen, Inc., Calif.). The anti-mouse CD40 MAb, designated FGK45, which is used in the experiments described below, is described by Rolink, A. et al. (1996 *Immunity* 5:319-330). Anti-human CD40 MAbs can be made following techniques well-known in the art, and described by Kohler et al. (1975 *Nature* 256:495-497). MAbs can be raised by immunizing rodents (e.g. mice, rats, hamsters and guinea pigs) with either native CD40 as expressed on cells or purified from human plasma or urine, or recombinant CD40 or its fragments, expressed in a eukaryotic or prokaryotic system. Other animals can be used for immunization, e.g. non-human primates, transgenic mice expressing human immunoglobulins and severe combined immunodeficient (SCID) mice transplanted with human B lymphocytes. Hybridomas can be generated by conventional procedures by fusing B lymphocytes from the immunized animals with myeloma cells (e.g. Sp2/0 and NSO), as described by Kohler et al. (1975 *Nature* 256:495-497). In addition, anti-CD40 MAbs can be generated by screening of recombinant single-chain Fv or Fab libraries from human B lymphocytes in phage-display systems. The specificity of the MAbs to CD40 can be tested by enzyme linked immunosorbent assay (ELISA), Western immunoblotting, or other immunochemical techniques.

For treating humans, the anti-CD40 MAbs would preferably be used as chimeric, deimmunised, humanized or human antibodies. Such antibodies can reduce immunogenicity and thus avoid human anti-mouse antibody (HAMA) response. It is preferable that the antibody be IgG4, IgG2, or other genetically mutated IgG or IgM which does not augment antibody-dependent cellular cytotoxicity (Canfield et al. 1991 *J. Exp. Med.* 173:1483-1491) and complement mediated cytolysis (Xu et al. 1994 *J. Biol. Chem.* 269:3469-3474; Pulito et al. 1996 *J. Immunol* 156:2840-2850).

Chimeric antibodies are produced by recombinant processes well known in the art, and have an animal variable region and a human constant region. Humanized antibodies have a greater degree of human peptide sequences than do chimeric antibodies. In a humanized antibody, only the complementarity determining regions (CDRs) which are responsible for antigen binding and specificity are animal derived and have an amino acid sequence corresponding to the animal antibody, and substantially all of the remaining portions of the molecule (except, in some cases, small portions of the framework regions within the variable region) are human derived and correspond in amino acid sequence to a human antibody. See, Riechmann et al. 1988 *Nature* 332:323-327; U.S. Pat. Nos. 5,225,539 and 5,530,101.

Deimmunised antibodies are antibodies in which the T and B cell epitopes have been eliminated, as described in International Patent Application PCT/GB98/01473. They have reduced immunogenicity when applied in vivo.

Human antibodies can be made by several different ways, including by use of human immunoglobulin expression libraries (Stratagene Corp., La Jolla, Calif.) to produce fragments of human antibodies (VH, VL, Fv, Fd, Fab, or $(Fab')_2$, and using these fragments to construct whole human antibodies using techniques similar to those for producing chimeric antibodies. Human antibodies can also be produced in transgenic mice with a human immunoglobulin genome. Such mice are available from Abgenix, Inc. (Fremont, Calif.), and Medarex, Inc. (Annandale, N.J.).

One can also create single peptide chain binding molecules in which the heavy and light chain Fv regions are connected. Single chain antibodies ("ScFv") and the method of their construction are described in U.S. Pat. No. 4,946,778. Alternatively, Fab can be constructed and expressed by similar means (Evans et al. 1995 *J. Immunol. Meth.* 184:123-138). All of the wholly and partially human antibodies are less immunogenic than wholly murine MAbs, and the fragments and single chain antibodies are also less immunogenic. All these types of antibodies are therefore less likely to evoke an immune or allergic response. Consequently, they are better suited for in vivo administration in humans than wholly animal antibodies, especially when repeated or long-term administration is necessary. In addition, the smaller size of the antibody fragment may help improve tissue bioavailability, which may be critical for better dose accumulation in acute disease indications, such as tumor treatment.

Based on the molecular structures of the variable regions of the anti-CD40 mAbs or the known CTL-activating peptides, one could use molecular modeling and rational molecular design to generate and screen molecules which mimic the molecular structures of the binding region of the antibodies or the peptides, respectively, and activate CTLs. These small molecules can be peptides, peptidomimetics, oligonucleotides, or other organic compounds. The mimicking molecules can be used for treatment of cancers and infections. Alternatively, one could use large-scale screening procedures commonly used in the field to isolate suitable molecules from libraries of compounds.

The dosage for the molecules of the invention can be readily determined by extrapolation from the in vitro tests and assays described below, or from animal experiments or from human clinical trials. The molecules of the invention would be preferentially administered by injection, in the case of antibodies or proteins.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

GM-CSF

GM-CSF used in the practice of the invention with human subjects includes any pharmaceutically safe and effective human GM-CSF, or any derivative thereof having the biological activity of human GM-CSF. In a presently preferred embodiment, the GM-CSF used in the practice of the subject methods is recombinant human GM-CSF (rhu GM-CSF), such as LEUKINE (immunex Corporation, Seattle, Wash.). LEUKINE is a biosynthetic, yeast-derived, recombinant human GM-CSF, consisting of a single 127 amino acid glycoprotein that differs from endogenous human GM-CSF by having a leucine instead of a proline at position 23. Other natural and synthetic GM-CSFs, and derivatives thereof having the biological activity of natural human GM-CSF, will of course be equally useful in the practice of the invention.

As the degree of glycosylation of biosynthetic GM-CSFs appears to influence half-life, distribution, and elimination, the most effective dose of GM-CSF for the subject methods may vary depending on the source used (Lieschke et al. 1992 *N. Engl. J. Med.* 327:28-35; Dorr, R. T. 1993 *Clin. Ther.* 15:19-29; Horgaard et al. 1993 *Eur. J. Hematol.* 50:32-36).

LEUKINE has been shown to exhibit the same hematopoietic effects as those induced by endogenous GM-CSF, namely, the stimulation of progenitor cells committed along the granulocyte-macrophage pathway to form neutrophils, monocytes, macrophages, and eosinophils (Technical Product Report: LEUKINE Liquid, Immunex Corp., Seattle, Wash., 1997, which is herein incorporated by reference). LEUKINE, like endogenous GM-CSF, also promotes the differentiation of progenitor cells giving rise to erythrocytes and megakaryocytes. In addition to stimulating hematopoiesis, LEUKINE enhances many of the functional activities of mature neutrophils, monocytes and macrophages, such as chemotaxis, growth factor secretion, anti-tumor activity, anti-bacterial and antifungal activities, etc.

The optimal dose, frequency of administration, and duration of treatment with GM-CSF which is effective in the practice of the invention may vary depending on the subject and may vary from patient to patient. Typically, however, a therapeutically effective doses of GM-CSF sufficient to enhance an immune response in a human subject will be greater than or equal to about 50 µg, preferably greater than or equal to about 100 µg, more preferably greater than or equal to about 150 µg, and most preferably greater than or equal to about 200 µg. GM-CSF may be administered as a one time dose or it may be administered over a period of a few hours, days or weeks.

Immunogen

As used herein, an immunogen refers to any compound which is capable of generating a specific immune response in a subject. The immunogen may comprise a whole organism, killed, attenuated or live; a subunit or portion of an organism; a recombinant vector containing an insert with immunogenic properties; a piece or fragment of DNA capable of inducing an immune response upon presentation to a host subject; a protein, a polypeptide, a peptide, an epitope, a hapten, or any combination thereof. Preferred immunogens are those comprising a CTL epitope.

Method for identifying CTL epitopes are described for example, in WO 2005/026192, U.S. Patent Publication No. 20050181458 and U.S. Pat. Nos. 6,838,269, 6,835,550, and 6,897,049.

Immunogens may be derived from infectious organisms or they may be cancer cell preparations. Immunogens may be preparations of components expressed on cancer cells or on cells infected with infectious organisms. Immunogens may be derived from infectious organisms including viral, bacterial, fungal or protozoic infectious organisms. For example viral organisms include HIV 1, HIV 2, hepatitis A, hepatitis B, hepatitis C, Epstein-Barr Virus (EBV), and human papillomaviruses, including for example, HPV 16 or HPV 18.

Tumor specific antigens include, for example, those encoded by the MAGE gene family, such as MAGE 1 and MAGE 3, GAGE, BAGE and RAGE. Other cancer-associated antigens arising from mutations, such as p53, K-ras, CDK4 and the bcl-c-ab1 gene product, antigens over-expressed in cancer cells, such as c-erb2 (or neu) protein; as well as oncogenic viral antigens, such as the E7 protein of HPV-16 are included. Oncofetal antigens, such as CEA (carcinoma embryonic antigen) or alpha-fetoprotein (AFP), as well as differentiation antigens, such as prostate specific antigen and CD-10 (CALLA antigen), which is expressed in B-cell leukemias and lymphomas, may also be employed.

In one embodiment of the invention the immunogen is derived from a human papillomavirus (HPV), preferably HPV 16 or 18. In one example, an HPV E7 polypeptide immunogen or/and HPV 16 E2 polypeptide immunogen is administered, preferably and HPV 16 E7 and/or an HPV 16 E2 immunogen. For example, the HPV E7 or E2 immunogens may be administered as part of an HPV virus like particle or they may be administered as peptides or polypeptides. When the HPV E7 or E2 immunogens are administered as part of a virus like particle, the virus like particle may comprise the complete E2 or E7 polypeptide sequence, or a fragment thereof. The fragments or portions preferably comprise at least one CTL epitope.

As used herein, an HPV E2 polypeptide or an HPV E7 polypeptide refers the complete polypeptide sequence for these proteins, or a portion thereof. Preferably, an HPV E2 polypeptide comprises at least 10, 20, 30, 50, 70, 100, 130, 160, or 200 contiguous amino acids of a naturally occurring HPV E2 polypeptide. Preferably, an HPV E7 polypeptide comprises at least 10, 20, 30, 50, 70, 100, 130, or 150. Preferably, E2 and E7 polypeptides are at least 70%, preferably 80%, more preferably at least 90%, and most preferably 95% homologous to a naturally occurring HPV polypeptide. It is specifically contemplated as part of the invention that E2 and E7 polypeptides, including those administered as a component of a VLP, may comprise a portion of a larger fusion protein.

HPV virus like particles have been described for example in the following references: Frazer 2002 Virus Res. 89:271-274; Pastrana 2001 Virology 279:361-369; Storni et al. 2002 J. Immunol. 168:2880-2886; Da Silva 2001 Int. Immunol 13:633-641). HPV virus like particles are also described in the following patent publications: U.S. Pat. No. 6,878,541, WO04052395; WO03031583; U.S.20030129728; WO02092796; WO0009699; WO0035478; U.S. Pat. No. 6,013,262; WO9950424; WO05032586; WO04056389; WO 03077942; U.S. Pat. No. 6,649,167; U.S. Pat. No. 6,562,351; U.S.20020193565; WO0045841A3; WO9961052; WO9420137.

In a preferred embodiment, the HPV E2 or E7 immunogen are administered as part of virus like particle as a fusion protein with at least a portion of the HPV L1 or L2 proteins, preferably the L2 protein.

In one embodiment, the HPV immunogens are administered as polypeptides or as nucleic acid molecules that encode polypeptides. In preferred embodiments, the polypeptides, either administered directly or indirectly via nucleic acid molecules, comprise CTL epitopes. In preferred embodiments, the polypeptides have "HLA-A2 binding activity", defined herein as specific binding affinity for HLA-A2 expressing cells.

It is specifically contemplated as one aspect of the invention that methods and compositions of the invention may be employed as part of a prime-boost protocol wherein a first vaccine composition that comprises the desired immunogen, a prime vaccine composition, is administered in conjunction with a boost vaccine composition that comprises a corresponding immunogen that differs in form from the immunogen of the prime vaccine composition.

The boost vaccine composition may be administered at the same time as the prime vaccine composition or it may be administered at some time following the initial administration of the prime vaccine composition. The prime and boost vaccine compositions may be administered via the same route or they may be administered via different routes. If the prime and boost vaccine compositions are administered at the same time they may be administered as part of the same formulation or as different formulations. Both the prime vaccine composition and the boost vaccine composition may be administered one or several times. Thus some doses of the prime vaccine may be administered after the administration of a dose of the boost vaccine. It is within the skill of one with ordinary skill in the art to optimize prime boost combinations, including the optimization of routes of vaccine administration and timing for vaccine administrations.

Preferred prime-boost combinations of the invention include, but are not limited to, the following exemplary combinations:

a prime vaccine composition comprising an HPV VLP that comprises an HPV E7 polypeptide and a boost vaccine composition comprising an HPV E7 polypeptide;

a prime vaccine composition comprising an HPV VLP that comprises an HPV E2 polypeptide and a boost vaccine composition comprising an HPV E2 polypeptide;

a prime vaccine composition comprising an HPV E7 peptide and a boost vaccine composition t comprising an HPV VLP that comprises an HPV E7 peptide;

a prime vaccine composition comprising an HPV E2 peptide and a boost vaccine composition t comprising an HPV VLP that comprises an HPV E2 peptide Administration of Vaccine Compositions of the Present Invention As used herein, the terms "co-administration" or "administration in conjunction with" refers to situations wherein the specified agents are administered as part of the same compositions or as separate compositions sufficiently close together in time and in sufficient proximity to each other to achieve the desired results.

It is contemplated as an aspect of the invention that the immunogens, CD40 agonists or GM-CSF agents may be administered directly, e.g. as proteins or polypeptides, or they may be administered as nucleic acid molecules that encode proteins or polypeptides.

It is also contemplated as an aspect of this invention that vaccine components may be administered to a subject ex-vivo. For example, nucleic acid molecules may be introduced ex vivo into cells, which cells are then introduced into the subject to be vaccinated. In a further example, an immunogen such as viral like particle or a peptide or a polypeptide may be administered ex vivo to dendritic cells, which cells are then introduced into the subject to be vaccinated. In preferred embodiments of ex vivo administration, the cells are derived from the subject to be vaccinated.

The vaccines of the present invention may be administered by inhalation, or intracavity (e.g., oral, vaginal, rectal, nasal, peritoneal, ventricular, or intestinal), intradermally, intramuscularly, intranasally, intraocularly, intraperitoneally, intrarectally, intratracheally, intravenously, orally, subcutaneously, transdermally, or transmucosally (i.e., across a mucous membrane) in a dose effective for the production of neutralizing antibody and resulting in protection from infection or disease. The present vaccine can generally be administered in the form of a spray for intranasal administration, or by nose drops, inhalants, swabs on tonsils, or a capsule, liquid, suspension or elixirs for oral administration. The vaccine may be in the form of single dose preparations or in multi-dose flasks, which can be used for mass vaccination programs. Reference is made to Genaro, A. O. "*Remington: the Science and Practice of Pharmacy*," Lippincott Williams & Wilkins (2005) and *New Trends and Developments in Vaccines*, Voller et al. (eds.), University Park Press, Baltimore, Md. (1978), for methods of preparing and using vaccines.

The vaccine compositions of the present invention can be lyophilized to produce a vaccine composition in a dried form for ease in transportation and storage. The vaccine compositions of the present invention may be stored in a sealed vial, ampule or the like. In the case where the vaccine is in a dried form, the vaccine is dissolved or suspended (e.g., in sterilized distilled water) before administration. An inert carrier such as saline or phosphate buffered saline or any such carrier, in which the vaccine composition has suitable solubility, may be used.

The immunogenic compositions of the invention can be formulated according to known methods for preparing pharmaceutical compositions, whereby the substance to be delivered is combined with a pharmaceutically acceptable carrier vehicle. Suitable vehicles and their preparation are described, for example, in Genaro, A. O. "*Remington: The Science and Practice of Pharmacy*." Lippincott Williams & Wilkins (2005).

The compositions of the present invention may be in the form of an emulsion, gel, solution, suspension, etc. In addition, the pharmaceutical composition can also contain pharmaceutically acceptable additives including, for example, diluents, binders, stabilizers, and preservatives.

The amount of polypeptides or nucleic acid molecules in a vaccine composition of the present invention depends on many factors, including the age and weight of the subject, the delivery method and route, the type of treatment desired, and the type of nucleic acid molecule being administered. The optimal amount of polypeptides or nucleic acid molecules of the invention that should be administered to a subject to induce an optimal immune response can be readily determined by one of skill in the art.

In general, a composition of the present invention containing nucleic acids contains from about 1 ng to about 30 mg of nucleic acid molecule or polynucleotide construct.

In general, a composition of the present invention containing an immunogenic protein or polypeptide contains from about 1 ng to about 30 mg of an immunogenic protein or polypeptide.

The vaccine compositions of the present invention may be used in concert with adjuvants and other compounds to enhance their immunologic effect. Adjuvants include, but are not limited to, various oil formulations such as stearyl tyrosine (ST, see U.S. Pat. No. 4,258,029), the dipeptide MDP, saponin, aluminum hydroxide, and lymphatic cytokine. Mucosal adjuvants include cholera toxin B subunit (CTB), a heat labile enterotoxin (LT) from *E. coli*, and Emulsomes (Pharmos, LTD., Rehovot, Israel). The adjuvant alum (aluminum hydroxide) or ST may be used for administration to humans.

For aqueous pharmaceutical compositions used in vivo, sterile pyrogen-free water is preferred. Such formulations will contain an effective amount of the substance together with a suitable amount of vehicle in order to prepare pharmaceutically acceptable compositions suitable for administration to a human or animal. Polynucleotides or polynucleotide constructs may be solubilized in a weak acid or weak base, and then diluted to the desired volume, for example, with an aqueous solution of the present invention. The pH of the solution may be adjusted as appropriate. In addition, a pharmaceutically acceptable additive can be used to provide an appropriate osmolarity.

Vaccine compositions of the invention may comprise nucleic acid molecules dissolved in a salt solution which improves entry of the polynucleotide or polynucleotide construct into vertebrate cells in vivo. Preferred salts in which to dissolve a polynucleotide or polynucleotide construct of the present invention include but are not limited to sodium phosphate, sodium acetate, sodium bicarbonate, sodium sulfate, sodium pyruvate, potassium phosphate, potassium acetate, potassium bicarbonate, potassium sulfate, potassium pyruvate, disodium DL-α-glycerol-phosphate, and disodium glucose-6-phosphate. "Phosphate" salts of sodium or potassium can be either the monobasic form, e.g., $NaHPO_4$, or the dibasic form, e.g., $Na_2HPO_4$, but a mixture of the two, resulting in a desired pH, is most preferred. The most preferred salts are sodium phosphate or potassium phosphate. As used herein, the terms "sodium phosphate" or "potassium phosphate," refer to a mixture of the dibasic and monobasic forms of each salt to present at a given pH.

Special Considerations Relating to the Administration of Nucleic Acid Vaccine Compositions of the Present Invention Numerous methods for delivering nucleic acid molecules are known in the art. The most convenient way to delivery the polynucleotide constructs is in a plasmid (DNA) vector. Alternatively, a viral vector can be used. A number of viral based systems have been developed for transfecting mammalian cells. For example, nucleic acid molecules of the invention can be inserted into a vector and packaged as retroviral particles using techniques known in the art. A number of retroviral systems have been described (U.S. Pat. No. 5,219, 740; Miller et al. 1989 *BioTechniques* 7:980-990; Miller 1990 *Human Gene Ther.* 1:5-14; and Burns et al. 1993 *PNAS USA* 90:8033-8037).

A number of adenovirus vectors have also been described (Haj-Ahmad et al. 1986 *J. Virol.* 57:267-274; Bett et al. 1993 *J. Virol.* 67:5911-5921; Mittereder et al. 1994 *Human Gene Ther.* 5:717-729; and Rich et al. 1993 *Human Gene Ther.* 4:461-476). Additionally, various adeno-associated virus (AAV) vector systems have been developed. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. 1988 *Molec. Cell. Biol.* 8:3988-3996; Vincent et al. 1990 *Vaccines* 90 (Cold Spring Harbor Laboratory Press); Carter, B. J. 1992 *Current Opin. Biotechnol.* 3:533-539; Muzyczka, N. 1992 *Current Topics Microbiol. Immunol.* 158:97-129; and Kotin 1994 *Human Gene Ther.* 5:793-801. Additional viral vectors, which will find use for delivering the recombinant nucleic acid molecules of the present invention, include, but are not limited to, those derived from the pox family of viruses, including vaccinia virus and avian poxvirus.

DNA vaccines and methods of their manufacture and delivery that may be used in accordance with the present invention are disclosed in U.S. Pat. Nos. 5,589,466; 5,620,896; 5,641,665; 5,703,055; 5,707,812; 5,846,946; 5,861,397; 5,891,718; 6,022,874; 6,147,055; 6,214,804; 6,228,844; 6,399,588; 6,413,942; 6,451,769, European Patent Documents EP1165140A2; EP1006796A1 and EP0929536A1; and PCT Patent Publications WO00/57917; WO00/73263; WO01/09303; WO03/028632; WO94/29469; WO95/29703; and WO98/14439.

Administration may be by needle injection, catheter infusion, biolistic injectors, particle accelerators (e.g., "gene guns" or pneumatic "needle less" injectors) Med-E-Jet (Vahlsing, H. et al. 1994 *J. Immunol. Methods* 171:11-22), Pigjet (Schrijver, R. S. et al. 1997 *Vaccine* 15:1908-1916), Biojector (Davis, H. L. et al. 1994 *Vaccine* 12:1503-1509; Gramzinski, R. et al. 1998 *Mol. Med.* 4:109-118), Advanta Jet (Lindmayer, I. et al. 1986 *Diabetes Care* 9:294-297), Medi-jector (Martins, J. K. et al. 1979 *J. Occup. Med.* 21:821-824), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, J. Y. et al. 1999 *Life Sciences* 65:2193-2203) or topical applications during surgery.

Thus, in one embodiment, administration is into muscle tissue, i.e., skeletal muscle, smooth muscle, or myocardium. Most preferably, the muscle is skeletal muscle. For polynucleotide constructs in which the polynucleotide or polynucleotide construct is DNA, the DNA can be operably linked to a cell-specific promoter that directs substantial transcription of the DNA only in predetermined cells.

The DNA vaccine may be administered (especially by injection) into tissue and voltage pulses applied between electrodes disposed in the tissue, thus applying electric fields to cells of the tissue. The electrically-mediated enhancement covers administration using either iontophoresis or electroporation in vivo. Suitable techniques of electroporation and iontophoresis are provided by Singh, J. et al. 1989 *Drug Des. Deliv.* 4:1-12; Theiss, U. et al. 1991 *Methods Find. Exp. Clin. Pharmacol.* 13:353-359; Singh and Maibach 1993 Dermatology 187:235-238; Singh, P. et al. 1994 *Crit. Rev. Ther. Drug Carrier Syst.* 11:161-213; Su, Y. et al. 1994 *J. Pharm. Sci.* 83:12-17; Costello, C. T. et al. 1995 *Phys. Ther.* 75:554-563; Howard, J. P. et al. 1995 *Arch. Phys. Med. Rehabil.* 76:463-466; Kassan, D. G. et al. 1996 *J. Amer. Acad. Dermatol.* 34:657-666; Riviere et al. 1997 *Pharm. Res.* 14:687-697; Zempsky, W. T. et al. 1998 *Amer. J. Anesthesiol.* 25:158-162; Muramatsu, T. et al. 1998 *Int. J. Mol. Med.* 1:55-62; Garrison J. 1998 *Med. Device Technol.* 9:32-36; Banga A. K. et al. 1998 *Trends Biotechnol.* 16:408-412; Banga A. K. et al. 1999 *Int. J. Pharm.* 179:1-19; Neumann E. et al. 1999 *Bioelectrochem. Bioenerg.* 48:3-16; and Heiser, W. C. 2000 *Methods Mol. Biol.* 130:117-134.

The nature of the electric field generated in accordance with such methods is determined by the nature of the tissue, the size of the selected tissue and its location. The use of insufficient or excessive field strength is to be avoided. As used herein, a field strength is excessive if it results in the lysing of cells. A field strength is insufficient if it results in a reduction of efficacy of 90% relative to the maximum efficacy obtainable. The electrodes may be mounted and manipulated in many ways known in the art. The waveform of the electrical signal provided by the pulse generator can be an exponentially decaying pulse, a square pulse, a unipolar oscillating pulse train or a bipolar oscillating pulse train. The waveform, electric field strength and pulse duration are dependent upon the type of cells and the DNA that are to enter the cells via electrical-mediated delivery and thus are determined by those skilled in the art in consideration of these criteria. Any number of known devices may be used for delivering the DNA vaccine and generating the desired electric field. Examples of suitable devices include, but are not limited to, a single needle probe, a bipolar probe and a combination needle and plate probe. Alternatively, methods such as continuous-flow electroporation may be employed (see, U.S. Pat. Nos. 6,485,961; 6,090,617; 6,074,605; 5,720,921; 5,612,207; and 5,098,843).

Nucleic acid molecules of the present invention, e.g., plasmid DNA, derivatives of plasmid DNA, mRNA, linear DNA, viral genomes, or polynucleotide fragments contained therein may be formulated into any of the various compositions and may be used in any of the methods disclosed herein. For aqueous compositions used in vivo, use of sterile pyrogen-free water is preferred. Such formulations will contain an effective amount of a polynucleotide or polynucleotide construct together with a suitable salt and/or auxiliary agent as disclosed herein, in order to prepare pharmaceutically acceptable compositions suitable for optimal administration to a vertebrate. Insoluble polynucleotides or polynucleotide constructs may be solubilized in a weak acid or weak base, and then diluted to the desired volume, for example, with an aqueous solution of the present invention. The pH of the solution may be adjusted as appropriate. In addition, a pharmaceutically acceptable additive can be used to provide an appropriate osmolarity.

The compositions of the present invention may include one or more transfection facilitating materials that facilitate delivery of polynucleotides or polynucleotide constructs to the interior of a cell, and/or to a desired location within a cell. Examples of the transfection facilitating materials include, but are not limited to lipids, preferably cationic lipids; inorganic materials such as calcium phosphate, and metal (e.g., gold or tungsten) particles (e.g., "powder" type delivery solutions); peptides, including cationic peptides, targeting peptides for selective delivery to certain cells or intracellular organelles such as the nucleus or nucleolus, and amphipathic peptides, i.e. helix forming or pore forming peptides; basic proteins, such as histones; asialoproteins; viral proteins (e.g., Sendai virus coat protein); pore-forming proteins; and polymers, including dendrimers, star-polymers, "homogenous" poly-amino acids (e.g., poly-lysine, poly-arginine), "heterogeneous" poly-amino acids (e.g., mixtures of lysine & glycine), co-polymers, polyvinylpyrrolidinone (PVP), and polyethylene glycol (PEG). Furthermore, those auxiliary agents of the present invention that facilitate and enhance the entry of a polynucleotide or polynucleotide construct into vertebrate cells in vivo, may also be considered "transfection facilitating materials."

Certain embodiments of the present invention may include lipids as a transfection facilitating material, including cationic lipids (e.g., DMRIE, DOSPA, DC-Chol, GAP-DLRIE), basic lipids (e.g., steryl amine), neutral lipids (e.g., cholesterol), anionic lipids (e.g., phosphatidyl serine), and zwitterionic lipids (e.g., DOPE, DOPC).

A cationic lipid that may be used in concert with the vaccine compositions of the present invention is a "cytofectin." As used herein, a "cytofectin" refers to a subset of cationic lipids that incorporate certain structural features including, but not limited to, a quaternary ammonium group and/or a hydrophobic region (usually with two or more alkyl chains), but which do not require amine protonation to develop a positive charge. Examples of cytofectins may be found, for example, in U.S. Pat. No. 5,861,397. Cytofectins that may be used in the present invention, include DMRIE ((±)-N-(2-hydroxyethyl)-N,N-dimethyl-2,3-bis(tetradecyloxy)-1-propanaminium bromide), GAP-DMORIE ((±)-N-(3-aminopropyl)-N,N-dimethyl-2,-3-bis(syn-9-tetradeceneyloxy)-1-propanaminium bromide), and GAP-DLRIE ((±)-N-(3-aminopropyl)-N,N-dimethyl-2,3-(bis-dodecyloxy)-1-propanaminium bromide).

The cationic lipid may be mixed with one or more co-lipids. The term "co-lipid" refers to any hydrophobic material that may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films. A preferred class of co-lipids is the zwitterionic phospholipids, which include the phosphatidylethanolamines and the phosphatidylcholines. Most preferably, the co-lipids are phosphatidylethanolamines, such as, for example, DOPE, DMPE and DPyPE. DOPE and DPyPE are particularly preferred.

Other hydrophobic and amphiphilic additives, such as, for example, sterols, fatty acids, gangliosides, glycolipids, lipopeptides, liposaccharides, neobees, niosomes, prostaglandins and sphingolipids, may also be included in the compositions of the present invention.

Having now generally described the invention, the same will be more readily understood through reference to the following examples, which are provided by way of illustration and are not intended to be limiting of the present invention unless specified.

EXAMPLE 1

Development of a Therapeutic Vaccine for HPV16 Using a Chimeric VLP Fusion Protein in Combination with GM-CSF and Anti-CD40

For the development of a combined prophylactic/therapeutic vaccine targeting both HPV 16 E7 and E2, a chimeric HPV 16 VLP was generated that incorporates an L2-E7E2 fusion protein into L1 VLPs (VLP-E7E2). It is different from published HPV16 chimeric VLPs, which incorporate either half of E7 as a C-terminal L1 fusion or full length E7 as a C-terminal fusion of L2 (Davidson, E. J. et al. 2003 *J. Gen. Virol.* 84:2089-2097; Greenstone, H. L. et al. 1998 *PNAS USA* 95:1800-1805). In mice these previous chimeric VLPs have been shown to induce HPV16 neutralizing antibodies (Greenstone, H. L. et al. 1998 *PNAS USA* 95:1800-1805; Pastrana, D. V. et al. 2001 *Virology* 279:361-369; Frazer, I. 2002 *Virus Res.* 89:271-274) and CTL response to E7 (Schafer, K. 1999 *Int. J. Cancer* 81:881-888). A vaccine strategy was identified to enhance CTL response to E7 and E2 using immune modulators and low dose chimeric VLP, 24 pmoles, without adjuvant in HLA-A2 transgenic mice (AAD). The data presented below show that the CD8+ T cell response induced by low dose VLP-E7E2 could be significantly enhanced using immune modulators. In addition, the strategies using different combinations of immunization priming and boosting with chimeric VLP-E7E2 and peptides were evaluated. The results are summarized in Table 1 below.

TABLE 1

| Primary Immunization | Secondary Immunization | T Cell Response | |
|---|---|---|---|
| | | E7 | E2 |
| VLP-E7E2 (24 pmoles) + GM-CSF & αCD40 | None | +++ | +/− |
| VLP-E7E2 (24 pmoles) + GM-CSF & αCD40 | IFA + E2 peptides (50 nmoles each) | No Data | +++ |
| IFA + E2 peptides (50 nmoles each) + GM-CSF & αCD40 | IFA + E2 peptides (50 nmoles each) | No Data | ++ |

Materials and Methods

Animals: Female C57BL/6 mice are purchased from Frederick Cancer Research Facility (National Institutes of Health, Frederick, Md.). All experiments were performed using AAD mice, a HLA-A2 transgenic strain of mouse (Newberg, M. H. et al. 1996 *J. Immunol.* 156:2473-2480). AAD mice expressing a chimeric HLA molecule comprising the alpha 1 and 2 domains of HLA-A*0201 with the alpha 3 domain of murine H-2Dd were bred from stock. Mice used in this study were 10 to 20 weeks of age and were maintained in a pathogen-free environment. All procedures with animals were carried out in accordance with institutionally approved protocols.

Immunization: Mice were immunized subcutaneously at the base of the tail with the chimeric VLPs. GM-CSF (Preprotech, Rocky Hill, N.J.) was given the day before and the same day as the VLP injection. Anti-CD40 (SouthernBiotech, Birmingham Ala.) was given with the VLP. Mice were also immunized with 50 nmoles of peptide in incomplete Freund's adjuvant (IFA) with or without GM-CSF (5 μg/mouse) and anti-CD40 (10 μg/mouse). All vaccines were prepared immediately prior to injection. Each group had 4 mice, and the pooled spleen cells from four mice were used for assays. 10 μg of VLP-E7E2 was given to a mouse. The MW of the VLP-E7E2 is about 5280 Kd (72×L1@55 Kd=3960 Kd, and 12×L2E7E2@110 kd=1320 Kd). The number of moles of VLP-E7E2 in 10 μg of total protein is about 24 pmoles.

VLP fusion protein: VLPs containing the full length L1 capsid gene of HPV16 strain 114K (Kirnbauer et al. 1993 *J. Virol.* 67):6929-6936) alone or with HPV16L2-E7-E2 were expressed in recombinant Baculovirus using the plasmid system (Shi, W. et al. 1999 *J. Virol.* 73:7877-7881). For 16KL1, a 1.5-kilobase Bgl II DNA fragment from pEnod-KL1 (Kirnbauer et al. 1993 *J. Virol.* 67:6929-6936) containing the HPV16 KL1 gene is cloned in the BamH1 site downstream of the polyhedrin promoter within the polh locus in the baculovirus donor plasmid pFastBac1 of the Bac-Bac Expression System (GIBCO BRL).

For the HPV16 L2-E7-E2 fusion gene, a full length HPV16 L2 gene, a full length HPV16 E7 gene with a Cys 24 point mutation/Rb binding defective (Barbosa, M. S. et al. 1990 *EMBO J.* 9:153-160) and a full length HPV16 E2 gene with a Gly 293 point mutation demyelization DNA binding defective (Prakash, S. S. et al. 1992 *Genes Dev.* 6:105-116) were fused 5' to 3' and cloned in the BamH1 site downstream of the polyhedrin promoter in the pFastBac vector. The L2 fragment is prepared by PCR with BamH1 and Cla1-Spe1 sites added at the 5' and 3' ends, respectively, through primer design. The sequence of the reverse primer is as follows: GGACTAGTT-TAGATCGATACATCTGAAAAAAAATATGG (SEQ ID NO: 3). The reverse primer creates a Cla1 site at the 3' end of L2 plus silent changes in the Val and Ser codons, a change from Leu to Ile in the terminal codon, a TAA stop codon, followed by a Spe1 site. After the L2 is joined to E7, the Ile at the C-term of L2 is eliminated. The E7 fragment with a Cys to Gly point mutation at amino acid 24 is prepared by overlapping PCR. BamH1-Cla1 and Cla-Spe1 sites are added to the 5' and 3' ends, respectively through primer design. The HPV16 E2 fragment with the Gly to Val point mutation at amino acid 293 is also prepared by overlap PCR. BamH1-Cla1 and Spe1 sites are added to the 5' and 3' ends, respectively through primer design. The BamH1/Cla1 L2 fragment, the Cla1 E7 fragment, the Cla1/Spe1 E2 fragment, and the BamH1/Spe1 pFastBac1 vector are ligated together. The ligation product is transformed into DH5 and clones are screened for the correct L2-E7-E2 order and orientation. The sequence of both the 16L2-E7-E2 and 16L1 genes are confirmed by DNA sequencing.

Expression and Purification of VLPs: VLPs containing 16 L1 with and without 16L2-E7-E2 were produced in Sf-9 cells. Sf-9 cells were infected with KL1 virus at an MOI of 3 for L 1 VLPs and with L1 and L2-E7-E2 virus at an MOI of 3 and 1, respectively for L1/L2-E7-E2 VLPs. Sf-9 cells were cultivated as a suspension culture in HyQ SFX-INSECT (Hyclone, Logan, Utah) in the presence of 10% FBS. VLPs were prepared using a modified version of Optiprep purification (Buck, C. B. et al. 2004 *J. Virol.* 78:751-757). Cells were lysed in the presence of protease inhibitors, mini complete (Roche, Mannheim, Germany) with 0.5% Brij58. Cellular DNA and RNA were degraded with 0.5% Benzonase and 0.2% Plasmid Safe (Epicentre, Inc., Madison, Wis.). Cell lysate was adjusted to 10 mM MgCl and incubated at room temperature for two hours. Then, NaCl was added to a final concentration of 0.8 M, and lysate incubated on ice for 10 more minutes. The lysate was first purified by 27.5% CsCl (wt/wt) equilibrium centrifugation for 20 hours at 28,000 rpm (Beckman, Fullerton, Calif.). Fractions Bands containing the VLPs were pooled and went through a second CsCl equilibrium centrifugation and VLP fractions dialyzed into two changes of PBS with 0.8 M NaCl. To further purify the VLPs for some experiments, fractions were collected and analyzed by SDS/PAGE after the first CsCl equilibrium centrifugation. Fractions containing the VLPs were pooled and dialyzed into two changes of DPBS with 0.8M NaCl and loaded onto a 27% to 39% Optiprep gradient in DPBS with 0.8M NaCl for 5 hours 35 minutes at 32,000 rpm and 16° C. in a SW-32 rotor. Fractions were collected and analyzed by SDS/PAGE. Fractions containing the VLPs were pooled and further purified in a Heparin Sepharose 6 Fast Flow column (Amersham Bioscience, Uppsala, Sweden.). Fractions from the Optiprep were diluted 10 fold in PBS, adjusted to a final concentration of 0.36M NaCl. The VLPs were then loaded on the Heparin column and washed with 10 bed volumes of PBS with 0.36 M NaCl. Virus-like particles was eluted using PBS containing 0.8M NaCl. Fractions were collected in polystyrene tubes and analyzed by SDS/PAGE. Fractions containing the VLPs were pooled.

Western Blots: Equal amount of VLPs samples and standards were run on SDS PAGE and transferred onto Immobilon-P for Western Blotting. Blots were stained with anti-HPV16L1 mAb (BD PharMingen), anti-16L2(5164), anti-16E2(BP47446), and anti-16E7(BP47445) for 16L1, 16L2, 16E2, and 16E7 detections, respectively.

Electron Microscopy: KL1 VLPs and Chimeric VLPs are negatively stained with 1% Uranyl Acetate and examined under the electron microscope Peptides, Cytokines and Antibodies: E7 49-57 (RAHYNIVTF) (SEQ ID NO: 4) for H-2 Kb, E7 11-20 (YMLDLQPETT) (SEQ ID NO: 5), E7 86-93 (TLGIVCPI) (SEQ ID NO: 6) and E2 69-77 (ALQAIELQL) (SEQ ID NO: 2) for HLA-A2 are obtained from Multiple Peptide Systems (San Diego, Calif.). mIL2 and mGM-CSF are purchased from Preprotech (Rocky Hill, N.J.), antibodies to CD40, CD40-FITC, CTLA-4, CD80-FITC, CD86-FITC, CD4 and CD8 are obtained from SouthernBiotech (Birmingham Ala.). Anti-CD16/CD32 (FcR) and CD11c-PE are from PharMingen (San Diego, Calif.). Anti-IFN-gamma and biotin anti-IFN-gamma are obtained from Mabtech (West Chester, Ohio).

Epitope Prediction and Peptide Synthesis: The sequences of HPV 16 E2 binding motif for HAL-A 2 were from NCBI. Two algorithms were employed to predict the epitope candidates binding to the HLA-A2 molecule: Bimas and Syfpeith. E7 11-20 (YMLDLQPETT, SEQ ID NO: 5), E7 86-93 (TL-GIVCPI, SEQ ID NO: 6), E2 69-77 (ALQAIELQL, SEQ ID NO: 2) E2 138-147 (YICEEASVTV, SEQ ID NO: 1) were synthesized by Multiple Peptide Systems (San Diego, Calif.).

CTL assay: Two (or three) weeks after immunization, spleens were aseptically removed and single cell suspensions are prepared. Erythrocytes were lysed in Tris-buffered ammonium chloride and the remaining cells are washed with complete T-cell medium (CTM), that is RPMI-1640 containing 10% FCS, 2 mM L-glutamine, penicillin (100 U/ml), streptomycin (0.1 mg/ml) and $5 \times 10^{-5}$ M 2-mercaptoethanol. Peptides (0.2 µM) are added to culture. T-stim (BD Biosciences) is added as a source of IL-2 to a final concentration of 10% on day 2 and day 4 in CTM. On day 6, CTM without T-stim is replaced with CTM, and cells are harvested on day 7 for the assay. EL-4 or C1R.ADD cells are used as target cells, and pulsed with or without peptides and $^{51}$Cr for 2 hours at 37° C. Cytolytic activity of cells is measured by a 4-h assay with $^{51}$Cr-labeled EL-4 or C1R.AAD target cells in triplicate wells. Percent $^{51}$Cr release is calculated as 100×(experimental release-spontaneous release)/(maximum release-spontaneous release). Maximum release is determined from supernatants of cells that are lysed by addition of percent Triton X-100. Spontaneous release is determined from target cells culture in medium. Data are expressed as an average from triplicate wells.

CD8 and CD4 Depletion: CD8 and CD4 positive cells are depleted using a Dynal CELLection™ Mouse CD4/CD8 Kit. Briefly, pre-washed Dynabeads coated with either anti-CD4 or CD8, are added to cell-suspension. After 20 minute incubation at room temperature (RT), the tube is placed in the Dynal MPC and the follow through is collected for the assays.

ELISPOT assay: The number of IFN-gamma-producing cells is also determined by ELISPOT assay. The anti-IFN-gamma antibody, 5 µg/ml, in PBS are coated on Millipore's multiscreen-HA plate (Millipore, Marlborough, Mass.) overnight at 4° C. The plate is blocked by incubation in RPMI containing 10% FCS for 3 hours at room temperature, and then the plate is washed two or three times with PBS. Target cells, EL-4 or C1R.ADD, are incubated with or without peptides for 2 hour at room temperature, washed twice. Then, they were placed at 5,000 per well. The effector cells were from 40,000 to 50,000 per well. After a 20 hour incubation period at 37° C., the plate is washed six times with PBS containing 0.05% Tween 20. The biotin-labeled anti-IFNgamma, at 2 μg/ml, is added to the plate. After a 3 hour incubation period at room temperature, the plate is washed six times, and developed using an ABC kit from Vector Lab (Burlingame, Calif.). The spots are counted using Immunspot™ CTL (Cleveland Ohio). Data are expressed as an average from triplicate wells.

Cytokine ELISA: Level of IFN-gamma, and IL-10 secretion are determined by Quantikine (R&D Systems, Minneapolis, N. Mex.). Spleen cells are cultured with or without peptide at the concentration of $5 \times 10^6$ cells/ml in a 24 well plate. Supernatants are collected on day 2, day 3 and day 4 for cytokine assay. The cytokine assays are performed following the manufacture's recommendation.

Antibody ELISA: IgG-Specific HPV16 L1 VLP-based enzyme-linked immunosorbent assays (ELISAs) are performed in a 96-well plate format. Briefly, 200 ng of HPV16L1 VLPs are plated per well and end point dilution titers are determined. Four-fold dilutions of each serum are assayed, starting at a dilution of 1:10. Sera are designated by ELISA positive at a given dilution if the optical density (OD) is greater than 0.2 and is at least double the reactivity of the same serum dilution in a well containing blocking buffer but no VLPs.

Flow cytometric analysis and Abs: Lymph node cells ($1 \times 10^6$) are taken from mice one week after immunization. Cells are blocked with rat anti-mouse CD16/CD32 (FcR) monoclonal antibody, and then stained for 30 min at 4° C. with the appropriate concentrations of mAbs in PBS containing 0.2% BSA and 0.1% $NaN_3$. Following two washes with PBS/BSA/$NaN_3$, cells are acquired using FACScan flow cytometers (BD Biosciences, Mountain View, Calif.). Data files are analyzed using CellQuest software (BD Biosciences, Mountain View, Calif.).

EXAMPLE 2

Characterization of Chimeric HPV 16 L1/L2-E7-E2 VLP Fusion Protein as a Therapeutic Vaccine for HPV16

Figure 2:
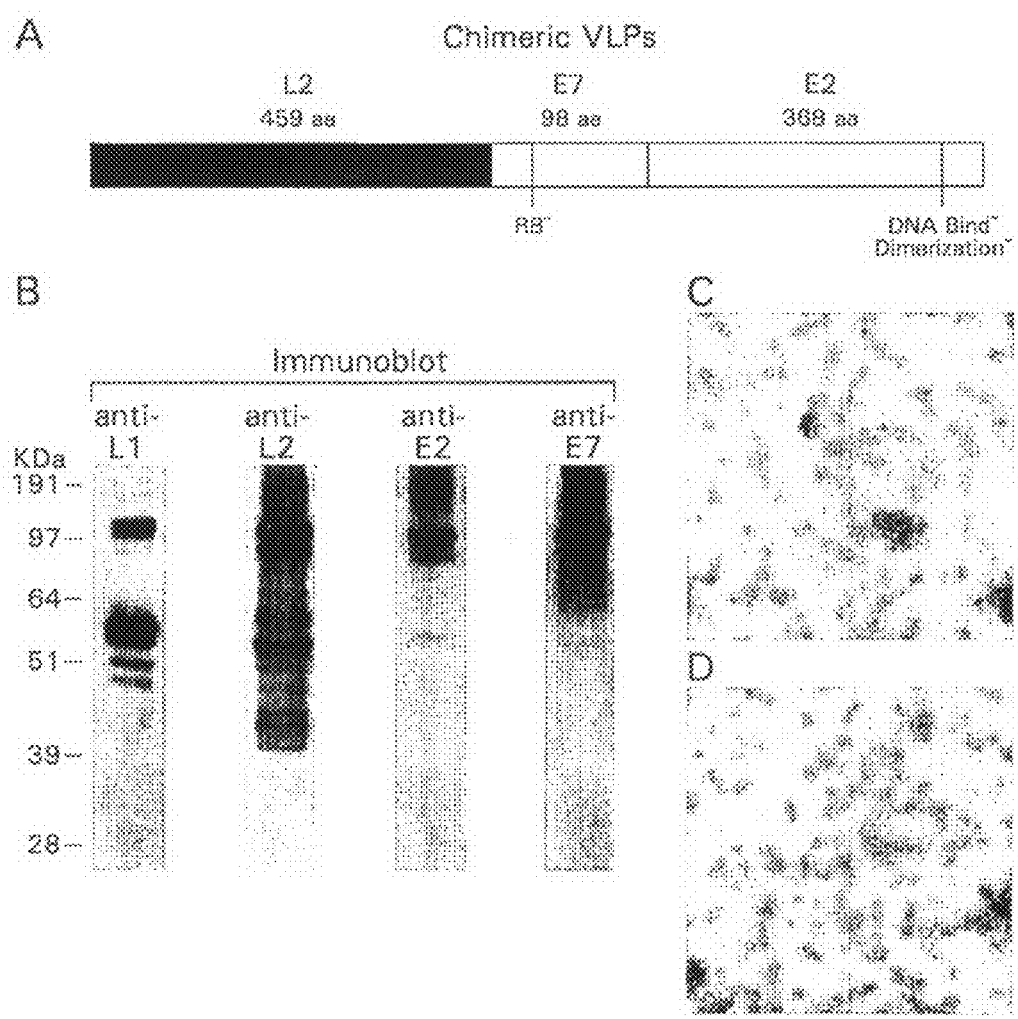
FIG. 2 shows chimeric L1-VLP-L2-E7-E2(VLP-E7 E2): Panel A is a schematic figure of chimeric VLP. Panel B is an analysis of VLP-E7E2 showing an SDS-PAGE/immunoblot analysis of the purified L1-VLP-L2-E7-E2 construct. The immunoblot was probed with anti-L1, L2, E2, and E7 antibodies. Purified chimeric were immuno-stained with anti-L1, L2, E2, and E7. Panel C shows an electron microscopy of the HPV16 L1 VLP construct (HPV16L VLPs). Panel D shows an electron microscopy of the chimeric L1-VLP-L2-E7-E2 construct (VLP-E7E2).

Characterization Of Chimeric HPV 16 L1/L2-E7-E2 VLP Fusion Protein (VLP-E7E2): HPV16 L1 VLP induces high titers of virus neutralizing antibodies and they are an attractive prophylactic vaccine candidate (Pastrana et al. 2001 *Virology* 279:361-369; Lowy, D. R. et al. 2003 *J. Natl. Cancer Inst. Monogr.* 111-116; Koutsky, L. A. et al. 2002 *N. Engl. J. Med.* 347:1645-1651). To increase the therapeutic potential of a VLP-based vaccine, a chimeric HPV16 VLP was generated. A schematic diagram of the chimeric construct is shown in FIG. 1. The chimeric construct included both the full length HPV16 E7 and full length HPV16 E2 as C-terminal extension of HPV16 L2 fusion protein (FIG. 2, Panel A and Panel B). The sequences of the both chimeric fusion proteins, VLP-L2E7E2 and VLP HPV16 L1 (L1-VLP), were confirmed by DNA sequencing. The protein expression and co-assembly of the L2 fusion protein into VLPs was confirmed by gradient centrifugation followed by Western blotting of the purified particles (FIG. 2, Panel C). Immunoblot of chimeric VLPs with anti-L1, L2, E2, and E7 indicated that all four proteins were present in the chimeric VLPs. Except for antibody to L1, antibodies to L2, E2 and E7 were polyclonal antibodies. The full length L2-E7-E2 is 104 KD. Some of the L2-E7-E2 had partially degraded as seen in the under 104 KD smear and bands in the L2 blot. There were some lower MW bands because there are sites in L2-E7-E2 that are more susceptible to proteolytic degradation. Despite of the partial degradation of the full length L2-E7-E2, Nevertheless, a good portion of full length L2-E7-E2 was incorporated into the VLPS, as indicated by the 104 KD band seen in the E2 and E7 blots. The chimeric VLPs were morphologically similar to L1-VLPs, as assessed by electron microscopic examination of negatively stained particles (FIG. 2, Panel C and Panel D).

The Chimeric HPV16 E7E2 VLP Protein Induces T Cell Responses to HPV 16 E7 in C57BL/6, but not in HLA-A2 Transgenic (AAD mice): The chimeric L1-VLP-L2-E7-E2 construct is analyzed with respect to the generation a T cell response in C57BL/6 and AAD mice. Mice are vaccinated with 10 μg of the L1-VLP-L2-E7-E2 construct, the L1 VLP construct (as a negative control), or E7 peptides with GM-CSF and IL-2 in IFA (as a positive control). Spleens are isolated and a CTL assay is performed after 7 days of in vitro stimulation with peptides (E7 49-57 for H-$2D^b$ cells and E7 11-20 and 86-93 for HLA-A2 cells). In C57BL/6 mice, cytolytic activity is detected with 10 μg of the L1-VLP-L2-E7-E2 construct, but not with 3 μg of the L1-VLP-L2-E7-E2 construct (FIG. 3, Panel A). 10 μg is the minimal dose to induce a CTL response in C57BL/6 mice in the experiments. However, the CTL response is not detected in AAD mice with immunized with 10 μg of the chimeric L1-VLP-L2-E7-E2 (FIG. 3, Panel B). The data indicated that the relevant E7 peptide of the chimeric L1-VLP-L2-E7-E2 construct could be processed in H-$2D^b$ mice to induce a CTL response in C57BL/6. However, response is not seen in AAD mice. To evaluate if HLA-A2 restricted peptides delivered by the chimeric L1-VLP-L2-E7-E2 can be processed, experiments were conducted to augment the L1-VLP-L2-E7-E2 induced CTL response via the administration of cytokines and antibodies to co-stimulatory molecules.

Figure 4:
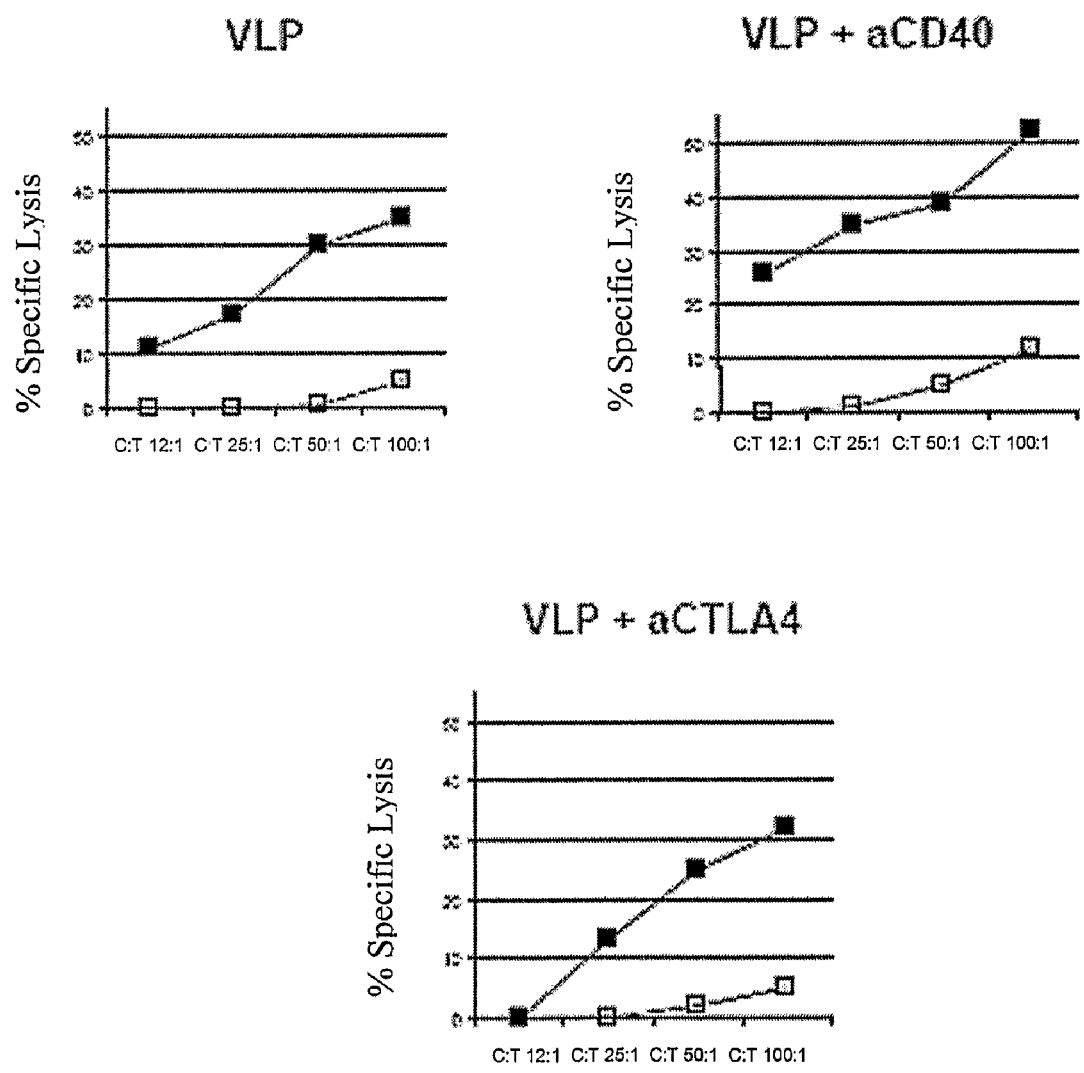
FIG. 4 shows an analysis of the augmentation of the L1-VLP-L2-E7-E2 induced CTL response in C57BL/6 mice with the indicated adjuvants. Splenic cells are taken two weeks after the initial immunization and re-stimulated with E7 49-57 peptides in vitro prior to the CTL assay. EL-4 target cells are pulsed with (closed squares) or without (open squares) the E7 49-57 peptides.
Figure 5:
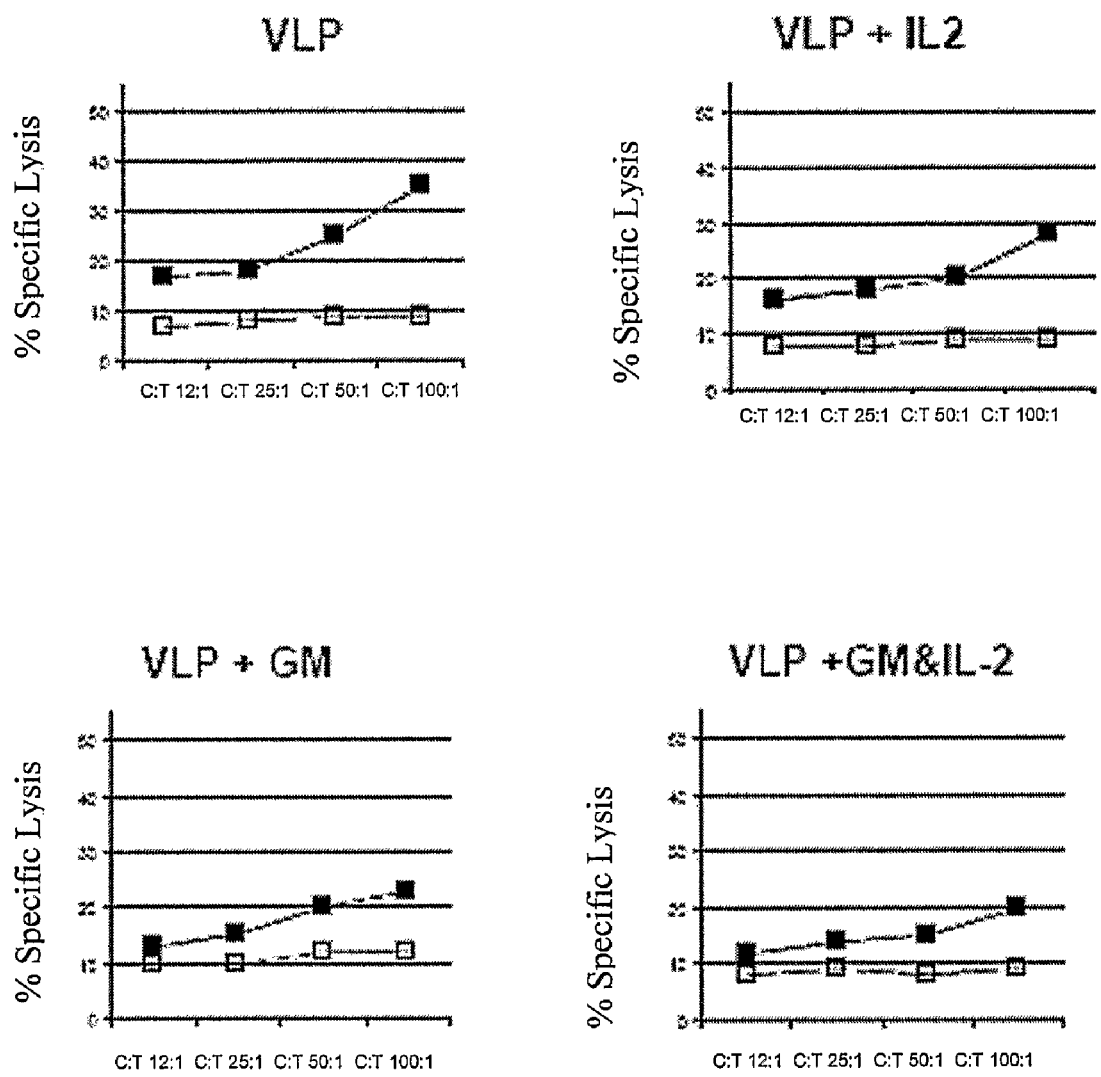
FIG. 5 shows an analysis of the augmentation of the L1-VLP-L2-E7-E2 induced CTL response in C57BL/6 mice with the indicated adjuvants. Splenic cells are taken two weeks after the initial immunization and re-stimulated with E7 49-57 peptides in vitro prior to the CTL assay. EL-4 target cells are pulsed with (closed squares) or without (open squares) E7 49-57 peptides.
Figure 6:
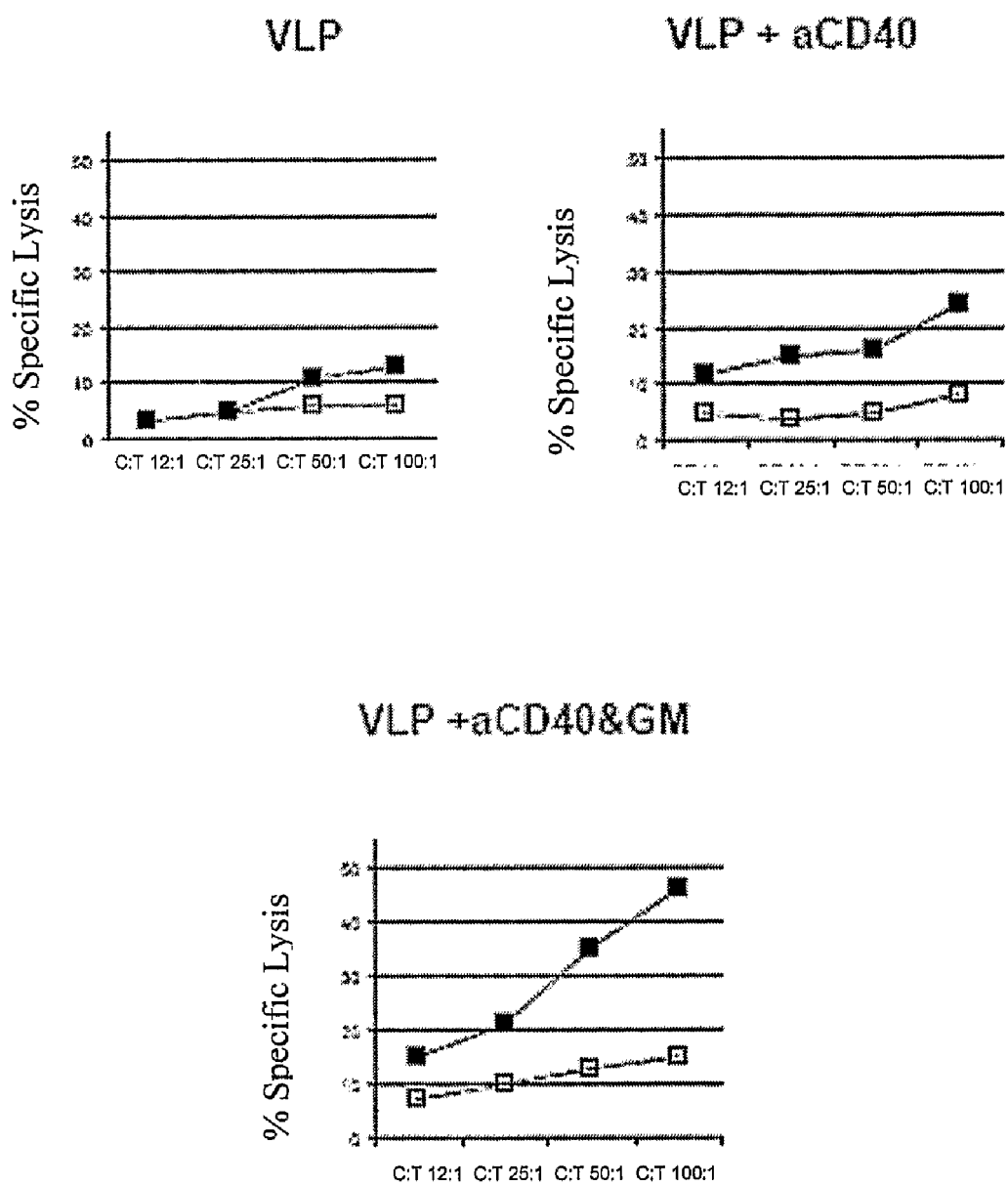
FIG. 6 shows an analysis of the augmentation of the L1-VLP-L2-E7-E2 induced CTL response in C57BL/6 mice with the indicated adjuvants. Splenic cells are taken two weeks after the initial immunization and re-stimulated with E7 49-57 peptides in vitro prior to the CTL assay. EL-4 target cells are pulsed with (closed squares) or without (open squares) E7 49-57 peptides.

Augmentation of chimeric VLP-E7E2 induced T cell response: To enhance L1-VLP-L2-E7-E2 induced T cell response, the effects of GM-CSF, IL-2, anti-CD40 antibody and anti-CTLA-4 antibody on enhancement of the T cell response were investigated initially in C57BL/6 mice. The concentration of GM-CSF and IL-2 to employ is determined in experiments to optimize peptide based vaccines. The concentration of anti-CD40 antibody is obtained from our previous publication (Ahlers et al. 2002 *PNAS USA* 99:13020-13025). These cytokines and antibodies are given in aqueous solution. As seen in FIG. 4, Panel A, the administration of anti-CD40 enhanced the VLP-E7E2 induced CTL response, but the administration of anti-CTLA-4 did not. GM-CSF, and IL-2 alone or GM-CSF plus IL-2 showed no effect on the VLP-E7E2 induced CTL response (FIG. 5). Two lots of VLP-E7E2 are used. The lot, which is used in the analysis represented in FIG. 6 showed some protein degradation in a gel electrophoresis analysis. This may explain the different level of CTL response observed in the first panels of FIGS. 4, 5, and 6. The data showed that GM-CSF and anti-CD40 acted synergistically in enhancing CTL response in vivo (FIG. 6).

Figure 7:
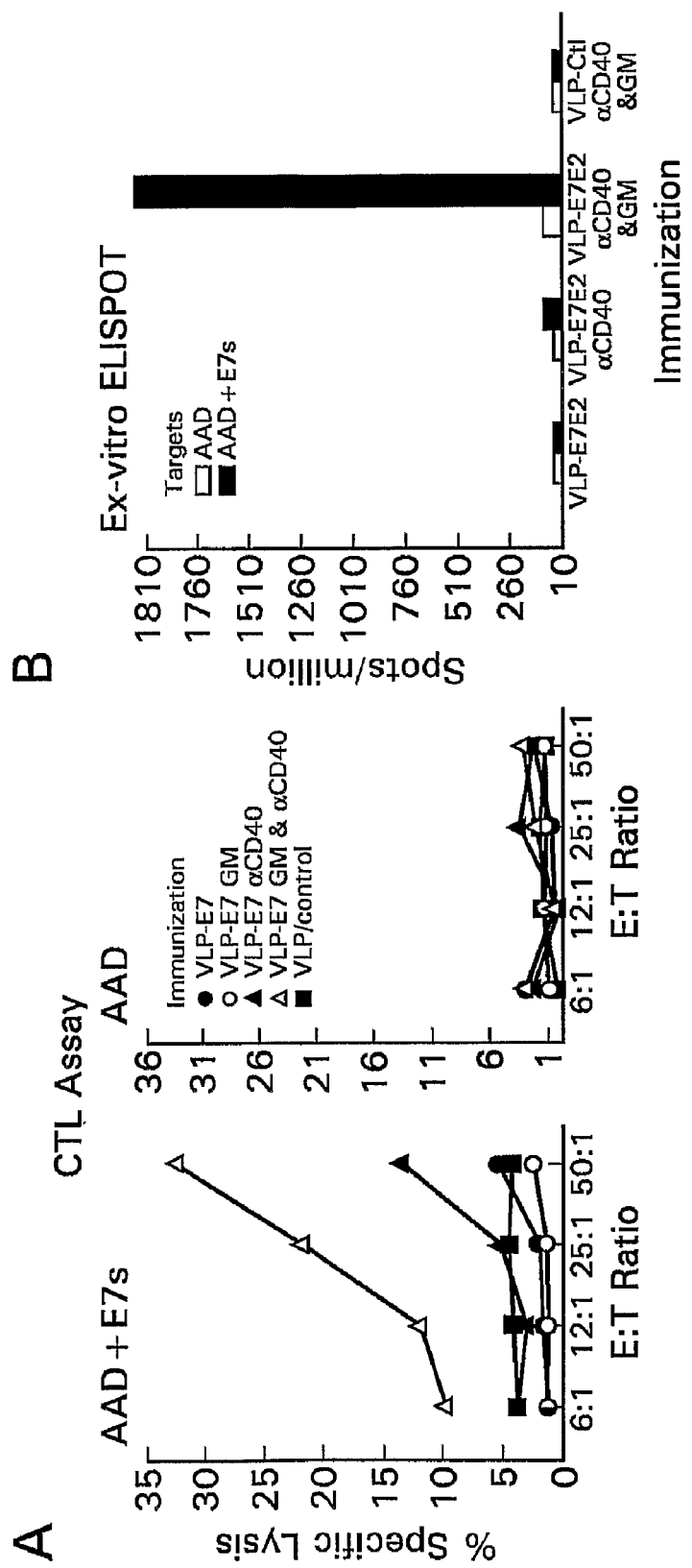
FIG. 7 shows an analysis of the augmentation of L1-VLP-L2-E7-E2 induced T cell response in HLA.A2 transgenic mice via the administration of GM-CSF and an anti-CD40 antibody. The figure shows augmentation of VLP-E7E2 induced T cell response in E7: Mice were immunized with different combinations of VLP-E7E2, GM-CSF and αCD40. Target cells, C1R.ADD, were pulsed with E7 11-20 and 86-93 as shown in Panel A. Panel B is the result of a parallel ex vitro ELISPOT assay, where C1R.ADD pulsed with or without E7 11-20 and 86-93 peptides were used as targets. Panel A shows the results of a CTL assay wherein spleen cells were incubated with target C1R.AAD cells pulsed with E7 11-20 and E7 86-93 peptides (left panel) or without peptides (right panel). Panel B shows the results of an ELISPOT assay using C1R.ADD target cells pulsed with or without E7 11-20 and E7 86-93 peptides.

Since the immune response to E7 is better characterized than the response to E2, first, several immunization regimens were examined for maximizing E7 responses in AAD mice. When mice were immunized with low dose, 10 μg (24 pmoles), of chimeric VLP-E7E2 without adjuvant, there was no detectable CTL response to E7 49-57 as shown in FIG. 7 (Panel A, Panel B). To enhance the VLP-E7E2-induced T cell response, several combinations of cytokine and antibodies were tested, such as GM-CSF, IL-2, anti-CD40 and anti-CTLA-4, which are known to induce T cell responses by either activating T cells or dendritic cell (DC) or down regulating negative signals. These cytokines and antibodies were co-injected in aqueous solution. The co-injection of anti-CTLA-4, GM-CSF, and IL-2 alone or GM-CSF plus IL-2 showed no effect on the VLP-E7E2-induced CTL response to E7. However, a significant CTL response to E7 was detected in AAD mice immunized with VLP-E7E2 in combination with GM-CSF and anti-CD40, without a traditional adjuvant, such as IFA. CTLA response was not detected in mice vaccinated with VLP-E7E2 alone or VLP-E7E2 with GM-CSF. The L1-VLP with GM-CSF and anti-CD40 was used as negative control (FIG. 7, Panel A). A weak but positive CTL response was seen in mice immunized with VLP-E7E2 with anti-CD40, but substantially less than in the group of mice immunized with GM-CSF and anti-CD40 (immune-modulators) (FIG. 7, Panel A). A parallel ELISPOT assay produced similar results (FIG. 7, Panel B). IFN-gamma producing cells were induced substantially in the mice that received VLP-E7E2/GM-CSF/anti-CD40. A weak response was found in mice that received VLP-E7E2 with anti-CD40, but not in mice that were immunized with VLP-E7E2 alone, or control L1-VLP with GM-CSF and anti-CD40. The data showed that GM-CSF and anti-CD40 acted synergistically and led to the best enhancing effect in vivo. These results provide guidance in enhancing CD8+ T cell responses in humans.

VLP-E7E2, in combination with GM-CSF and anti-CD40 generates CTL response in HLA-A2 transgenic mice: The protocol that is found to enhance L1-VLP-L2-E7-E2 induced CTL response in C57BL/6 mice is tested in AAD mice. A significant CTL responses to E7 peptides is detected in AAD mice immunized with the L1-VLP-L2-E7-E2/GM-CSF/anti-CD40 antibody combination, but not in mice immunized with the L1-VLP-L2-E7-E2 construct alone, the L1-VLP-L2-E7-E2 construct with GM-CSF, or L1-VLP/GM-CSF/anti-CD40 antibody as a negative control (FIG. 7, Panel A). A weak but positive CTL response is also seen in mice immunized with the L1-VLP-L2-E7-E2 construct in combination with the anti-CD40 antibody, but the response observed is substantially less than the response observed when GM-CSF and anti-CD40 antibody are used in combination (FIG. 7, Panel A). A parallel ELISPOT assay produced similar results (FIG. 7, Panel B). IFN-gamma producing cells are induced substantially only in mice that received the L1-VLP-L2-E7-E2/GM-CSF/anti-CD40 antibody combination. A weak response is observed in mice that received the L1-VLP-L2-E7-E2 construct in combination with the anti-CD40 antibody, but not in mice that are immunized with the L1-VLP-L2-E7-E2 construct alone or with an L1-VLP/GM-CSF/anti-CD40 antibody as a control. These results provide a guide for enhancing HLA restricted responses in humans.

T cell response augmented by GM-CSF and anti-CD40 is CD8 dependent: To determine if the augmentation of T cell response by immune modulators is CD8+ T-cell dependent, mice are immunized with the L1-VLP-L2-E7-E2 construct, with or without the combination of GM-CSF and anti-CD40. The spleens are taken two weeks after immunization, and spleen cells are stimulated in vitro for 7 days. CD4+ and CD8+ positive cells are depleted on day 7, prior to the conduction ELISPOT and CTL assays. In the ELISPOT assay, approximately 2000 spots are detected in mice immunized with the L1-VLP-L2-E7-E2 construct/GM-CFS/anti-CD40 antibody combination versus the detection of 167 spots when CD8+ cells are depleted prior to the assay (FIG. 8, Panel A). When CD4+ cells are depleted, the numbers of IFN-gamma producing cells remain high at 1600 spots. The slight reduction in the number of spots in the CD4+ depleted population could be explained by the loss of cells during the cell purification process. A parallel CTL assay confirmed that the cytolytic activity is also CD8+ dependent (FIG. 8, Panel B).

Figure 9:
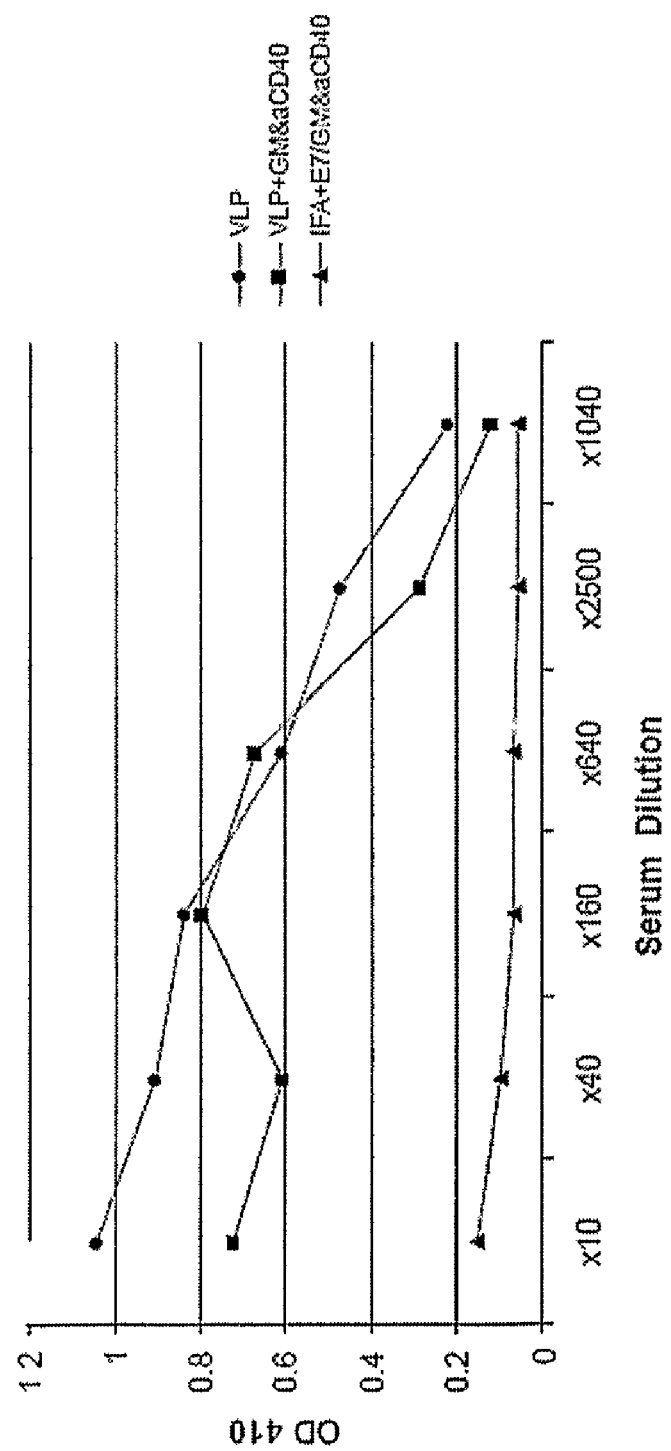
FIG. 9 shows an antibody response to L1 VLP in HLA.A2 transgenic mice immunized with the following preparations: (circles)—L1-VLP-L2-E7-E2; (squares)—L1-VLP-L2-E7-E2+GM-CSF+an anti-CD40 antibody+IFA; (triangles)—E7 peptides+GM-CSF+an anti-CD40 antibody+IFA. Mice were immunized with VLP-E7E2, L1-VLP and E7 peptides with GM-CSF and αCD40 in IFA emulsion. Serum was taken 18 days after immunization for ELISA assay. Antibody response was detected by ELISA.

Development of Antibody Response to L1-VLP: To analyze the effect of the GM-CSF/anti-CD40 antibody combination on antibody response, an ELISA assay was employed to measure the titre of anti-L1-VLP antibodies in mice immunized with the chimeric L1-VLP-L2-E2-E7 construct, with or without the GM-CSF/anti-CD40 antibody combination. Both groups of mice produced high titers of anti-L1 VLP antibodies (FIG. 9). There is no detectable anti-L1 VLP antibody in the serum of mice immunized with E7 peptide in combination with GM-CSF and anti-CD40 in IFA, as expected. The use of GM-CSF and an anti-CD40 antibody combination can increase the therapeutic potential of a HPV chimeric L1-VLP-E7-E2 vaccine by enhancing the induction of a CTL response to E7 without compromising the potential of the construct to induce L1-specific neutralizing antibodies as a prophylactic vaccine. To confirm the prophylactic potential of the chimeric L1-VLP-L2-E7-E2 construct, the anti body titers raised against the chimeric L1-VLP-E7 E2 construct and the L1-VLPs were compared using a recently developed quantitative HPV16 pseudovirus neutralization assay. Neutralizing titers in two rabbits vaccinated with the chimeric L1-VLP-L2-E7-E2 construct are 40,960 and 40,960, and they are 40,960 and 163,840 for two rabbits vaccinated with the L1-VLP construct. Therefore the chimeric L1-VLP-L2-E7-E2 construct retained the ability to induce high titers of neutralizing antibodies.

To test whether the combination of VLP-E7E2 with immune-modulators affects the antibody response, the titer of anti-L1-VLP antibodies was evaluated by ELISA. AAD mice were immunized with chimeric VLP-E7E2 with GM-CSF and anti-CD40, or L1-VLP. Both groups of mice produced similar titers of anti-L1 VLP antibodies (FIG. 9). There was no detectable anti-L1 VLP in mice immunized with E7 peptide in combination with immune-modulators in IFA, as expected. To confirm the prophylactic potential of the chimeric VLPs, we compared the antibody titers raised against the chimeric VLP-E7E2 and wild type VLPs, using a recently developed quantitative HPV16 pseudovirus neutralization assay. Neutralizing titers in two rabbits vaccinated with the chimeric VLPs were 40,960 compared to 163,840 for two rabbits vaccinated with the wild type VLPs. Therefore the chimeric VLPs retained the ability to induce high titers of neutralizing antibodies. Therefore, GM-CSF and anti-CD40 increased the therapeutic potential of a HPV chimeric VLP vaccine without compromising the VLPs potential to induce L1-specific neutralizing antibodies as a prophylactic vaccine.

T Cell Response Induced By Chimeric VLP-E7E2, GM-CSF And Anti-CD40 Is Not Due To The Suppression Of Systemic Reduction Of IL-10: Liu, X. S. et al. (2003) has reported that IL-10 play an important role in VLP immunized mice by suppressing CD8+ cells activities (Liu, X. S. et al. 2003 *J. Immunol.* 171:4765-4772). To determine if the absence of a CTL response to E7 is due to a suppression effect by IL-10, and to test the role of IL-10 in the immunization protocol, the level of IL-10 production was analyzed using spleen cells derived from immunized C57BL/6 mice. Spleen cells were cultured with E7 peptide, and supernatant was collected at 48, 72 and 96 hours. The results are shown in FIG. 10. IFN-gamma production was used as a positive control for the cytokine ELISA and was detected in mice immunized with VLP-E7E2 and IFA-E7 in immune-modulators (VLP-E7E2/GM-CSF/anti-CD40 and IFA+E2E7/GM-CSF/anti-CD40), which is in agreement with the results of the CTL and ELISPOT assay. IFN-gamma production increased over time in the culture and at 96 hours was highest in the group receiving VLP-E7E2 (VLP-E7E2/GM-CSF/anti-CD40). In the IL-10 ELISA, 245 ng/ml of IL-10 was detected from mice immunized with VLP-E7E2 in immune-modulators (VLP-E7E2/GM-CSF/anti-CD40), only marginally higher than that from medium alone, 175 ng/ml. No increase in IL-10 secretion was detected from mice immunized with VLP-E7E2 and IFA-E2E7 in immune-modulators. The data indicate that GM-CSF and anti-CD40 have no effect on systemic production of IL-10.

DCS Play An Important Role In VLP-E7E2/GM-CSF/Anti-CD40 Induced CTL Response In Vivo: It is known that GM-CSF and anti-CD40 play important roles in DC activation (Gurunathan, S. et al. 1998 J. Immunol. 161:4563-4571; Ahlers, J. D. et al. 1997 PNAS USA 94:10856-10861). However, most studies of DC activation used an in vitro culture system. In the Examples reported herein, the phenotypic changes of DC in the draining lymph nodes (DLN) of vaccinated mice were analyzed. DLN cells were collected six days after vaccination and stained with antibodies to CD11c, and DC activation markers, such as CD40, CD80 and CD86, as shown in FIG. 11. The total percentage of CD11c+ cells was increased to 12.15% in mice immunized with VLP-E7E2/GM-CSF/anti-CD40 from 5.9% in mice receiving VLP-E7E2 alone. Likewise, the CD11c+ and CD40+double positive DCs were increased to 7.35%, compared with 2.85% of VLP-E7E2 immunized mice. The level of CD11c and CD40 double positive cells in mice vaccinated with chimeric VLP-E7E2 alone was similar to that in IFA alone. The combination of GM-CSF and anti-CD40 also increased the fraction of CD11c+ cells expressing CD80 and CD86, suggesting maturation of the DCs. A moderate increase in CD11c+ and CD40+ double positive cells was also observed in mice vaccinated with VLP-E7E2 with anti-CD40. In contrast, GM-CSF alone showed no effect on the recruitment or activation of the DCs in VLP-E7E2 immunized mice. In the above-described protocol, GM-CSF is given in an aqueous solution, which differs from others where GM-CSF is given in IFA emulsion or engineered into a tumor cell line (Ahlers, J. D. et al. 2001 Int. Immunol. 13:897-908). This explains the difference of the ability of GM-CSF in recruiting and activating DCs. The data indicates that the recruitment and activation of dendritic cells are key factors to augment VLP-E7E2 induced T cell response in vivo.

EXAMPLE 3

Characterization of E2 Proteins as a Therapeutic Vaccine for HPV16

Figure 12:
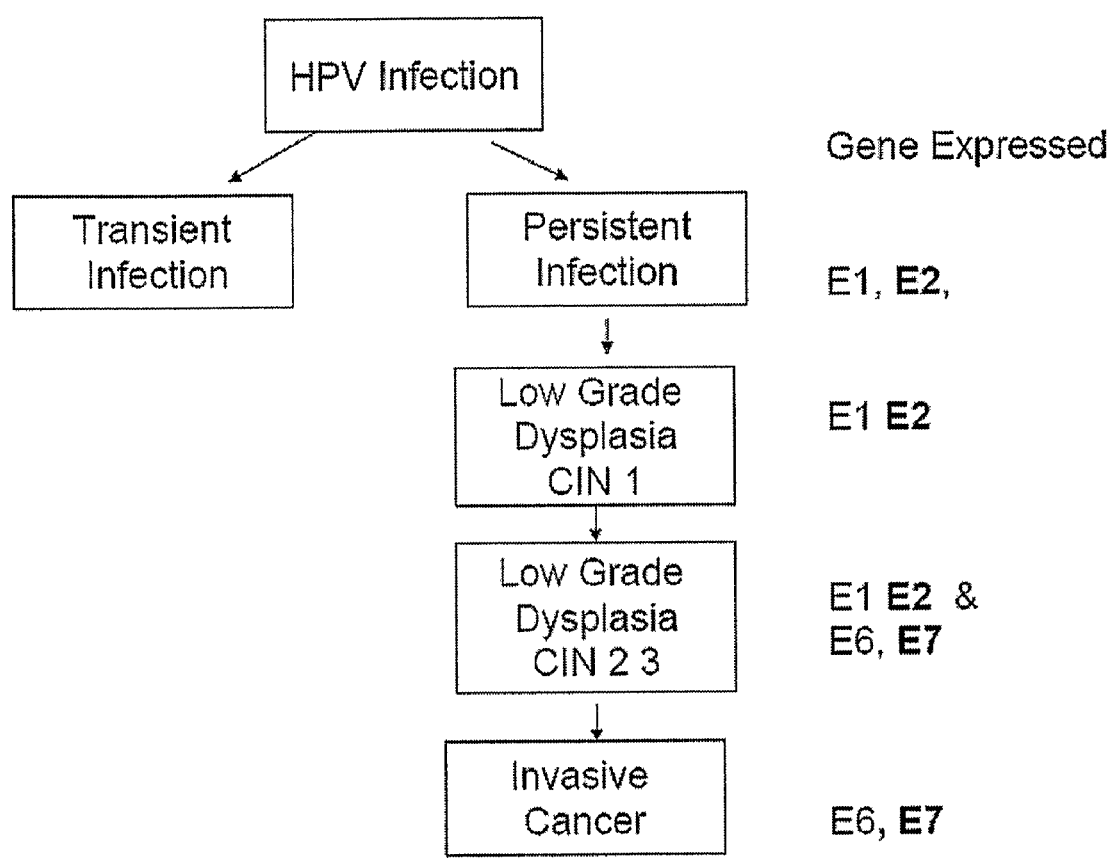
FIG. 12 is a schematic diagram of HPV 16 gene expression during persistent infection and disease progression in precancerous and cancerous cells.

Induction of CD8+ T Cell Response to HPV16 E2 μl HLA-A2 Transgenic Mice The HPV16 E2 gene is uniformly expressed during the productive viral infection (FIG. 12). Therefore, development of a vaccine targeting E2 may benefit not only the treatment of low-grade diseases caused by HPV infection, such as CIN, VIN, and AIN, and thereby prevent the subsequent development of HPV-associated anogenital cancers. Efforts have been made in identifying antibodies and CD4+ T cell response to HPV 16 E2. However, there is only limited information on the CD8+ T cell response to E2, which is important in eliminating HPV infection.

In order to induce a CD8+ T cell response to HPV 16 E2, E2 peptides containing an HLA-A2 binding motif are identified using the HLA-peptide binding prediction software of BIMAS (BioInformatics and Molecular Analysis Section, National Institutes of Health, Bethesda, Md.; and the SYF-PFHI database for the prediction of binding motifs. Four peptides were identified as shown in Table 2 below.

TABLE 2

| Position | Sequencing Residue | Score from BIMAS | Score from SYFPFTHI |
|---|---|---|---|
| E2 138-147 (SEQ ID NO: 1) | YICEEASVTV | 180 | 26 |
| E2 69-77 (SEQ ID NO: 2) | ALQAIELQL | 21 | 20 |
| E2 7-16 (SEQ ID NO: 7) | RLNVCQDKIL | 8.8 | 20 |
| E2 93-101 (SEQ ID NO: 8) | TLQDVSLEV | 285 | 19 |

Figure 13:
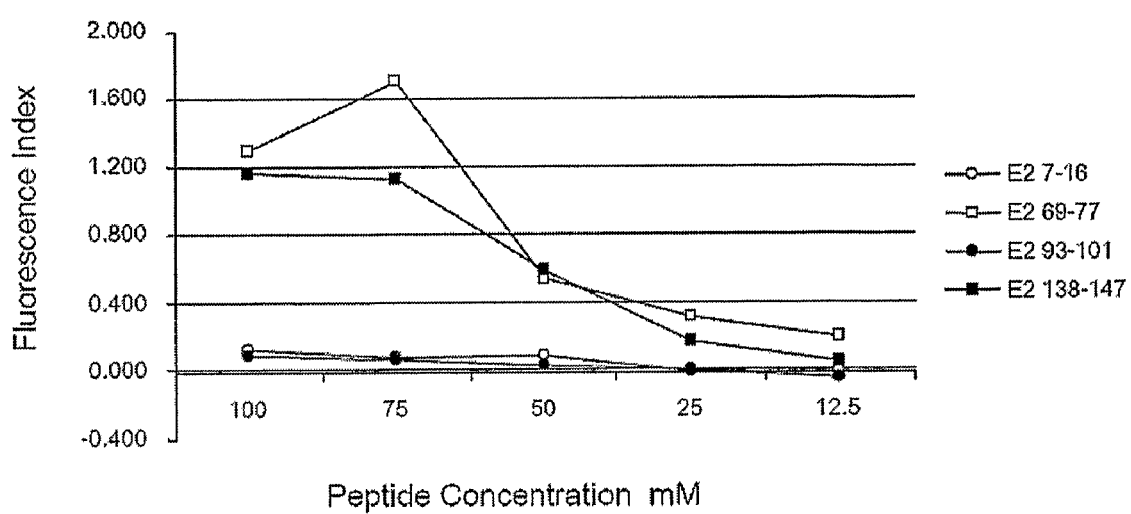
FIG. 13 shows an analysis of the binding of four E2 peptides with HLA.A2 binding motifs to HLA.A2 expressing cells. The sequences are derived from HPV 16 E2. T2 cells were loaded with various concentrations of peptides. Level of surface class I molecules were assessed by flow cytometric analysis using mouse monoclonal antibodies specific for HLA-A2. Fluorescence index=Fluorescence after peptide stimulation/Fluorescence without peptide −1.
Figure 14:
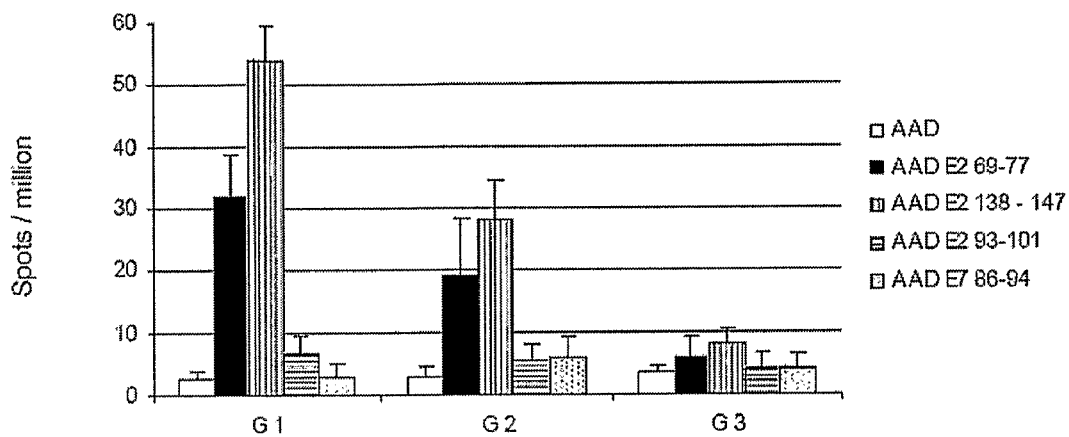
FIG. 14 shows the results of an ELISPOT assay of three immunization protocols for mice immunized with E2 peptides. AAD Mice were immunized with three E2 peptides. E2 69-77, E2 138-147 and E2 93-101, with or without, GM-CSF and αCD40. A target cell, C1R.ADD, was pulsed with peptides. C1R.ADD alone was used as negative control, and E7 86-93 was used as a specificity control. Mice are immunized with the indicated $1^{st}$ immunization and are then given the indicated $2^{nd}$ immunization (booster immunization) four weeks later. The G1, G2, and G3 immunization protocols employed are as follows: G1 ($1^{st}$ immunization: IFA+GM-CSF+anti-CD40 antibody+E2 peptides; $2^{nd}$ immunization: IFA+E2 peptides); G2 ($1^{st}$ immunization: IFA+GM-CSF+anti-CD40 antibody+E2 peptides; 2 immunization: none); G3 ($1^{st}$ immunization: none; $2^{nd}$ immunization: IFA+E2 peptides). The results show that the E2 peptides 69-77 and 138-147 are immunogenic and induce a CD8+ T cell response to E2 when administered in conjunction with GM-CSF and an anti-CD40 antibody.
Figure 15:
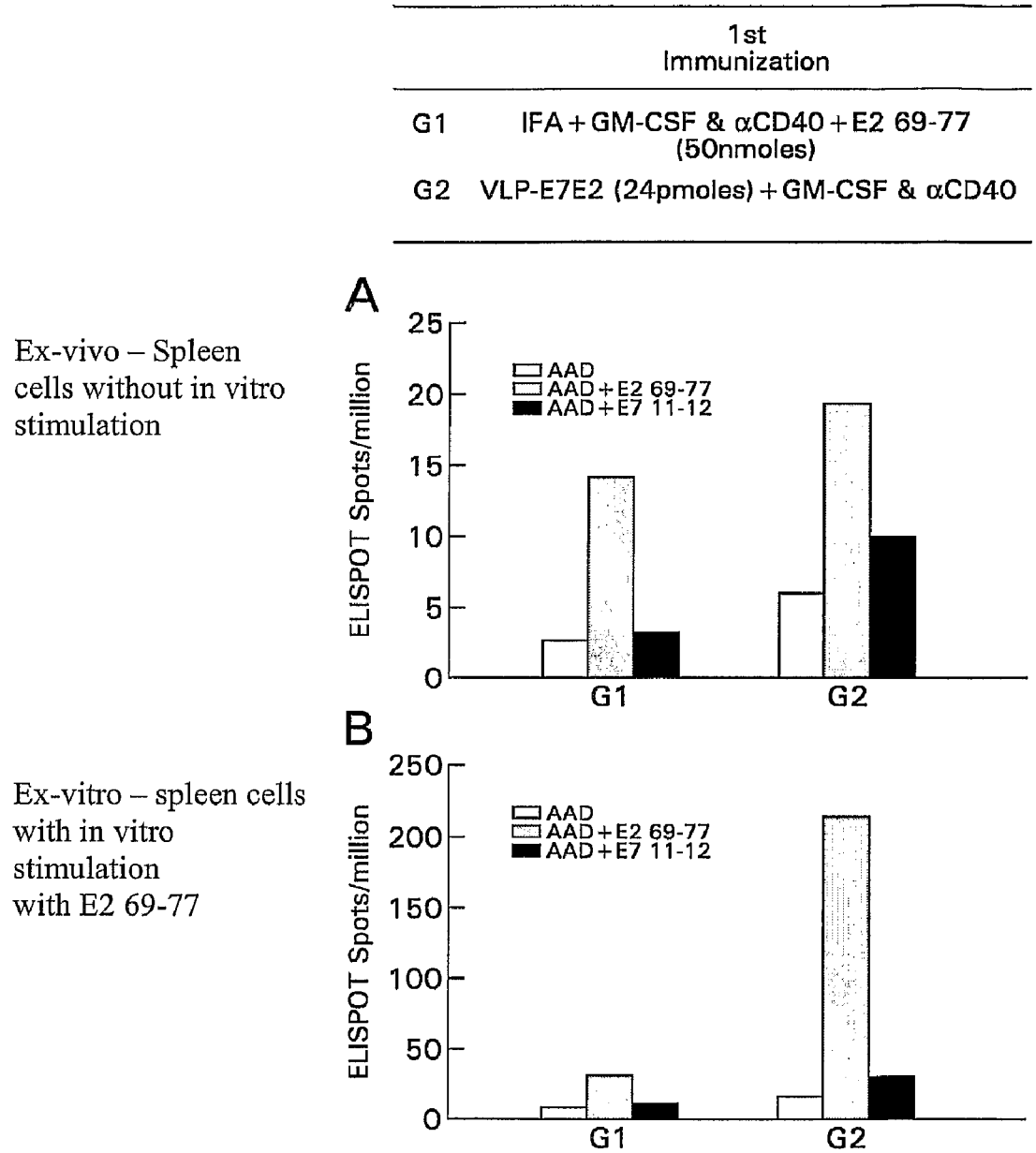
FIG. 15 shows the results of an ELISPOT assay of T-cell responses in mice immunized with the E2 69-77 peptide (50 nM) versus mice immunized with the L1-VLP-L2-E2-E7 construct (0.1 µM). AAD Mice were immunized with different combinations of VLP-E7E2 and E2 peptides with/without Gm-CSF and αCD40. Target cells were pulsed with E2 peptide. Immunization with E7 11-20 peptides is used as a control. The G1 and G2 immunization protocols employed are as follows: G1 ($1^{st}$ immunization: IFA+GM-CSF+anti-CD40 antibody+E2 69-77 peptides); G2 ($1^{st}$ immunization: L1-VLP-L2-E2-E7+GM-CSF+anti-CD40 antibody). Panel A shows the results obtained when fresh spleen cells, without in vitro stimulation, are employed to test T cell response, whereas Panel B shows the results obtained when spleen cells are stimulated with the E2 69-77 peptide in vitro for seven days prior to testing for T-cell response. The results show that a T-cell response to E2 can be induced by the L1-VLP-L2-E7-E2 construct and that the VLP construct is more efficient then the peptide in the induction of a T-cell response.
Figure 16:
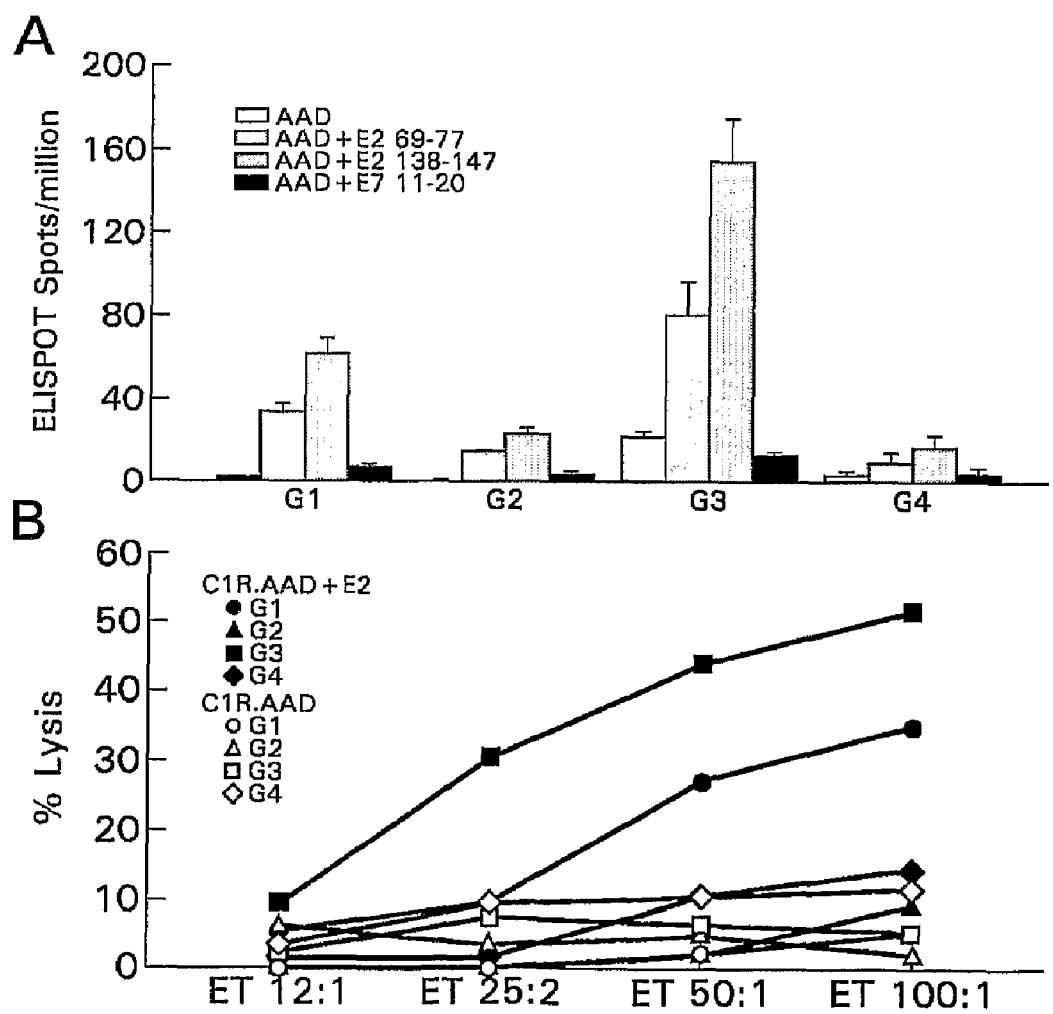
FIG. 16 shows the results of an ELISPOT assay of T-cell responses in mice immunized with E2 peptides in the following immunization protocols: G1 ($1^{st}$ immunization: IFA+GM-CSF+anti-CD40 antibody+E2 69-77 peptides; $2^{nd}$ immunization: IFA+E2 69-77 peptides); G2 ($1^{st}$ immunization: none; $2^{nd}$ immunization: IFA+GM-CSF+anti-CD40 antibody+E2 69-77 peptides); G3 ($1^{st}$ immunization: L1-VLP-L2-E7-E2+GM-CSF+anti-CD40 antibody; $2^{nd}$ immunization: IFA+E2 69-77 peptides); G4 ($1^{st}$ immunization: none; $2^{nd}$ immunization: L1-VLP-L2-E7-E2+GM-CSF+anti-CD40 antibody). Target cells are C1R.ADD cells pulsed with the indicated peptides. ELISPOT assay used fresh spleen cells as shown in Panel A. Panel B is the result of CTL assay where the spleen cells were stimulated 14 days in vitro with E2 peptides (E2 69-77, E2 138-147). Open symbols are target cells without peptides as negative control, and closed symbols are target cells pulsed with E2 69-77 and E2 138-147.
Figure 17:
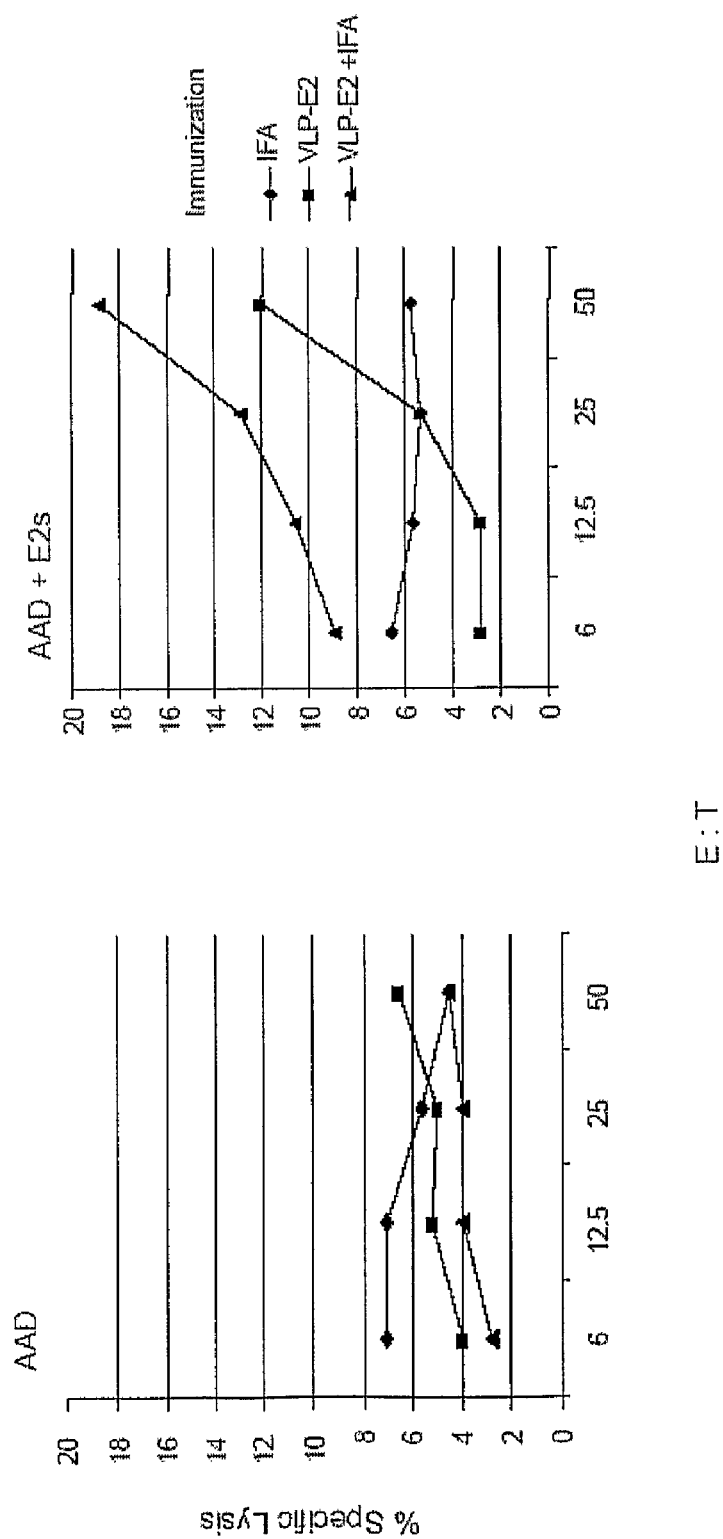
FIG. 17 shows the results of a CTL assay of T-cell responses in mice immunized with the following protocols: (triangle)—immunization with L1-VLP-L2-E7-E2+GM-CSF+anti-CD40 antibody and boosted with IFA+E2 peptides; (diamond)—immunization with IFA+E2 peptides; (square)—immunization with L1-VLP-L2-E7-E2+GM-CSF+anti-CD40-antibody. The panel on the left shows the results obtained with target C1R.ADD cells that are not pulsed with peptides (a negative control), and the panel on the right shows the results obtained with target C1R.ADD cells that are pulsed with E2 peptides.
Figure 18:
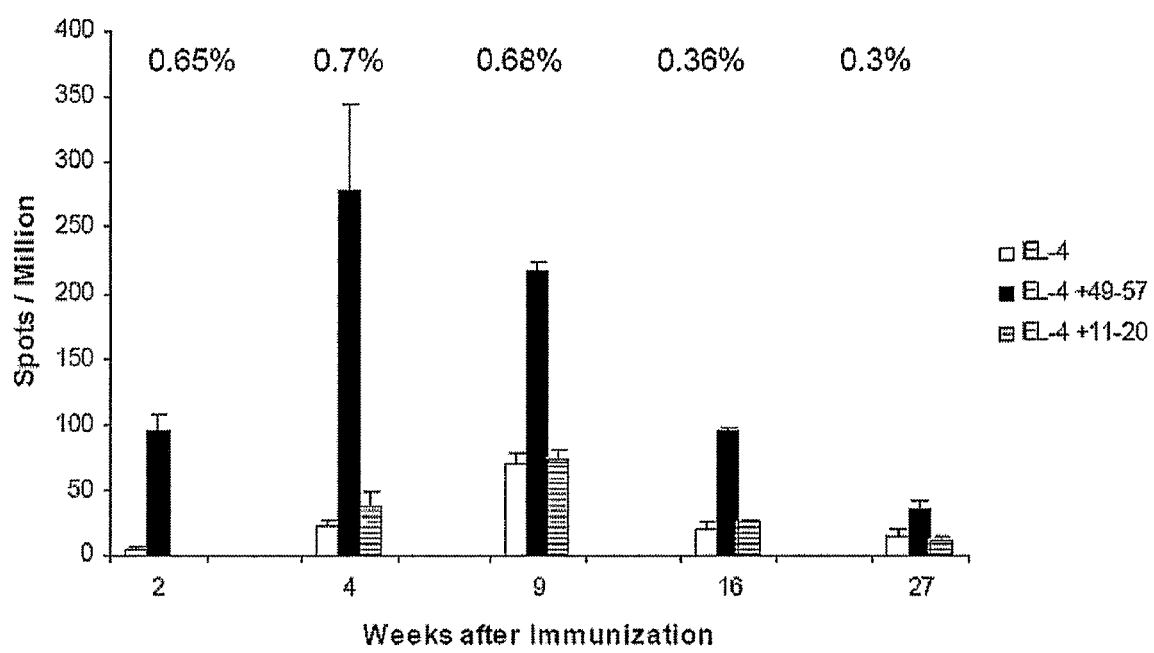
FIG. 18 shows the results of an ELISPOT assay of T-cell responses in mice immunized with E7 49-57 peptides, wherein spleen cells are removed at varying time points after immunization. EL-4 target cells are pulsed with E7 49-57 peptides or, as a control, E7 11-20 peptides.

Two of the peptides, E2 69-77 and E2 138-147, show a high binding affinity to HLA-A2 (FIG. 13). These two peptides also induce a CD8+ T cell response in HLA-A2 mice immunized with the E2 peptides, in combination with GM-CSF and an anti-CD40 antibody in an IFA emulsion, and boosted by the peptides in an IFA emulsion four weeks after the initial immunization (FIG. 14). The cytolytic T-cell response to the E2 peptides is also shown in FIG. 15. The data in Example 1 above show that immunization of mice with chimeric viral-like particles containing an E7 and E2 fusion protein (VLP-E7E2) in combination with GM-CSF and anti-CD40 induce a significant CD8+ T cell response to E7 but only a marginal CD8+ T cell response to E2. However, when mice are boosted with E2 peptides after a chimeric VLP prime, a strong CD8+ T cell response to E2 was detected (FIGS. 16, 17 and 18). Immunization protocols of using VLP-E7E2 and E2 peptides in an IFA emulsion are compared, as summaried in the Table 3 below.

TABLE 3

| Primary Immunization | 2<sup>nd</sup> immunization | T cell Response E7 | T cell Response E2 |
|---|---|---|---|
| VLP-E7E2 + GM-CSF + aCD40 | none | +++ | +/− |
| VLP-E7E2 + GM-CSF + aCD40 | IFA + E2 peptides | *ND | +++ |
| IFA + E2 peptides + GM-CSF + aCD40 | IFA + E2 peptides | *ND | ++ |

*ND indicates that data is not available

It is found that a primary immunization with VLP-E7E2 with immune-modulators (GM-CSF and anti-CD40 antibody) in an IFA emulsion generated a stronger immune response in comparison to a primary immunization of E2 peptides with immune modulators (GM-CSF and anti-CD40 antibody) in an IFA emulsion. These data indicate that E2 peptides are processed from chimeric VLP-E7E2 and presented by HLA-A2 molecules to generate CD8+ T cell responses. These data indicate a vaccine potential of VLP-E7E2 for low-grade disease caused by HPV infection. For example for disease at the CIN1 or CIN 2 stage after HPV 16 infection of cervical cells.

The anti-CD40 not only enhance the CD8+ T cell response to an antigen weeks after immunization, but generate lasting immune up to six month after an immunization (FIG. 18). The memory T cell response was tested by ELISPOT assay, shown as bar graph, and by tetramer staining, shown as % of antigen specific CD8+ T cells, using fresh isolated spleen cells. Our data demonstrated that there are 0.3% antigen specific tetramer positive cells six months after signal immunization with anti-CD40.

The mechanisms of antiCD40 induce lasting immunity was analyzed by purification of CD11c positive from immunized mice. FIG. 19 showed immunochemistry staining of IL-15, which is known cytokine that help the generation of memory CD8+ T cell. Our data showed that anti-CD40 could enhance the protein level of IL-15 in DCs from Immunized mice.

Induction of CD8+ T Cell Response to E2 Peptides. AAD mice were immunized with 50 mmoles of each E2 peptide, E2 69-77, E2 138-147 and E2 93-101 in combination with GM-CSF and anti-CD40 antibodies in IFA emulsion. One group of mice was boosted with E2 peptides in IFA emulsion (IFA-E2) two weeks later. An IFN-gamma ELISPOT assay was performed using spleen cells collected either two or four weeks after vaccination as shown in FIG. 14. The immunization protocol is shown in Table 4 below (50 nmoles of each immunogen was employed; "E2s" refers to E2 peptides).

TABLE 4

| | 1st Immunization | 2nd Immunization |
|---|---|---|
| G1 | IFA + GM-CSF & αCD40 + E2s | IFA + E2 peptides |
| G2 | IFA + GM-CSF & αCD40 + E2s | None |
| G3 | None | IFA + E2s |

The mice that received two immunizations displayed the highest number of IFN-gamma producing cells. The E2 138-147 was more immunogenic, with 53 spot/million, than E2 69-77, with 32 spots/million, despite the fact that both peptides displayed similar binding affinity to HLA-A2. The E2 93-101 did not bind to HLA-A2, and did not elicit a T cell response as expected. A second immunization with peptides in GM-CSF and anti-CD40 antibodies elicited a stronger T cell response than IFA-E2 alone. However, the second immunization with GM-CSF and anti-CD40 often causes a skin lesion, and most of the mice had likely to be euthanized before the end of experiment. Therefore, a second immunization with peptide in IFA without GM-CSF and anti-CD40 is preferable.

Identification of HLA.A2 Binding Epitopes front HPV 16 E2: Using the combination of immunogens: VLP-E7E2/GM-CSF/anti-CD40, a low level of CD8+ T cell response to E2 was detected as shown in FIG. 13. Since little was known about the MHC class I epitopes for E2, HLA-A2 binding sequences derived from HPV 16 E2 were investigated. Four HPV 16 E2 peptides, E2 7-16, E2 69-77, E2 138-147, and E2 93-101 were selected based on the prediction using two computer programs, Bimas and SYFPEITH, and our experience with the HLA-A2 binding motif. These peptides were synthesized and the sequences and locations are presented in Table 2. To test the binding affinity of these peptides to HLA-A2, a T2 binding assay was performed. The T2 cell expresses HLA-A2 and is TAP1 and TAP2 deficient. The binding of peptide to HLA-A2 on the T2 cell stabilizes the class 1 molecule, and then the level of HLA-A2 expression was measured using anti-HLA-A2 antibody and showed as FI values as described in Materials and Methods. Although four E2 peptides had sequence predicted to bind to HLA-A2, only two of them, E2 69-77 and E2 138-147, displayed binding ability to HLA-A2 (FIG. 13). Both E2 peptides exhibited similar low binding affinity with a FI 0.5 equal at a concentration of 50 μM. E2 7-16 and E2 93-101 showed no binding activity to T2 cells. The binding experiment was repeated three times with similar findings, since E2 93-101 was previously reported as a HLA-A2 binding epitope (Konya, J. et al. 1997 *J. Gen. Virol.* 78:2615-2620).

Enhancing CTL Response to E2. The amount of 50 nmoles of E2 peptide was used in the above-described peptides vaccines, because 25 nmoles of E2 peptides did not induce a detectable CTL response in AAD mice under the conditions employed. When AAD mice were immunized with either 50 nmoles E2 69-77 with immune modulators in IFA or 24 pmoles of VLP-E7E2 with immune-modulators in aqueous solution, a marginal CD8+ T cell response to E2 was detected by ELISPOT assay using fresh isolated spleen cells from both groups of mice (FIG. 15, Panel A and Panel B). However, the CD8+ T cell response could be significantly enhanced by in vitro stimulation of spleen cells with E2 peptide, especially in the group of mice that received 24 pmoles of VLP-E7E2 immune-modulators. The data indicated that E2 69-77 was a naturally processed sequence from HPV 16 E2 in the VLPs. A similar result was found for E2 138-147 (FIG. 16, Panel A and Panel B). The data from in vitro re-stimulation indicated that the CTL response to E2 might be enhanced by boosting in vivo.

Boosting of CTL responses to chimeric can be limited by existing anti-VLP antibodies induced in the primary immunization (Da Silva, D. M. 2001 *Int Immunol.* 13:633-641), the strategy of combination of chimeric VLP-E7E2 prime and E2 peptides vaccine boosting was examined (FIG. 16, Panel A and Panel B). The immunization protocol is shown in Table 5 below (50 nmoles of each immunogen was employed, unless otherwise indicated; "E2s" refers to E2 peptides).

TABLE 5

| | 1st Immunization | 2nd Immunization |
|---|---|---|
| G1 | IFA + GM-CSF & αCD40 + E2s | IFA + E2 peptides |
| G2 | None | IFA + GM-CSF & αCD40 + E2s |
| G3 | VLP-E7E2 (24 pmoles) + GM-CSF & αCD40 | IFA + E2s |
| G4 | None | VLP-E7E2 (24 pmoles) + GM-CSF & αCD40 |

Two groups of mice were boosted with E2 peptides in IFA without immune modulators (IFA-E2) four weeks after the initial immunization. The combination of 24 pmoles VLP-E7E2 with immune-modulators followed with E2 peptides immunization elicited stronger IFN-gamma production than two immunizations with peptides. E2 138-147 was more immunogenic than 69-77 (FIG. 16, Panel A). A parallel CTL assay was performed (FIG. 16, Panel B). CIR ADD cells pulsed with E2 69-77 and 138-147 were used as target cells. A CTL response was detected in the groups of mice that received two immunizations, but not in the mice given a single immunization of either the chimeric VLPs or the E2 peptides (FIG. 16, Panel B). Furthermore, primary immunization of VLP-E7E2 in immune-modulators followed by IFA-E2 peptides generated a better immune response, compared to mice with a primary immunization of IFA-E2 in immune-modulators and boost with IFA-E2 peptides. The data indicated that E2 peptides were processed from chimeric VLP-E7E2 and presented by HLA-A2 molecules to generate CD8+ T cell responses. Primary immunization using VLP-E7E2 generated a better immune response to E2 than primary immunization using E2 peptides, despite the difference in the amount of material used in the protocol, 0.24 vs. 50 nmoles respectively. The data indicated the vaccine potential of VLP-E7E2 for low-grade disease caused by HPV infection.

EXAMPLE 4

Modified HPV E2 Sequence Having Improved Immunogenicity

The above-described HPV 16 E2 gene sequence was evaluated in an effort to identify related sequences having enhanced capabilities to serve as a treatment or vaccine for HPV and HPV infection. The sequence of SEQ ID NO: 1 was modified to form a new peptide (SEQ ID NO: 9):

SEQ ID NO: 1: YICEEASVTV

SEQ ID NO: 9: YLAEEASVTV

Figure 21:
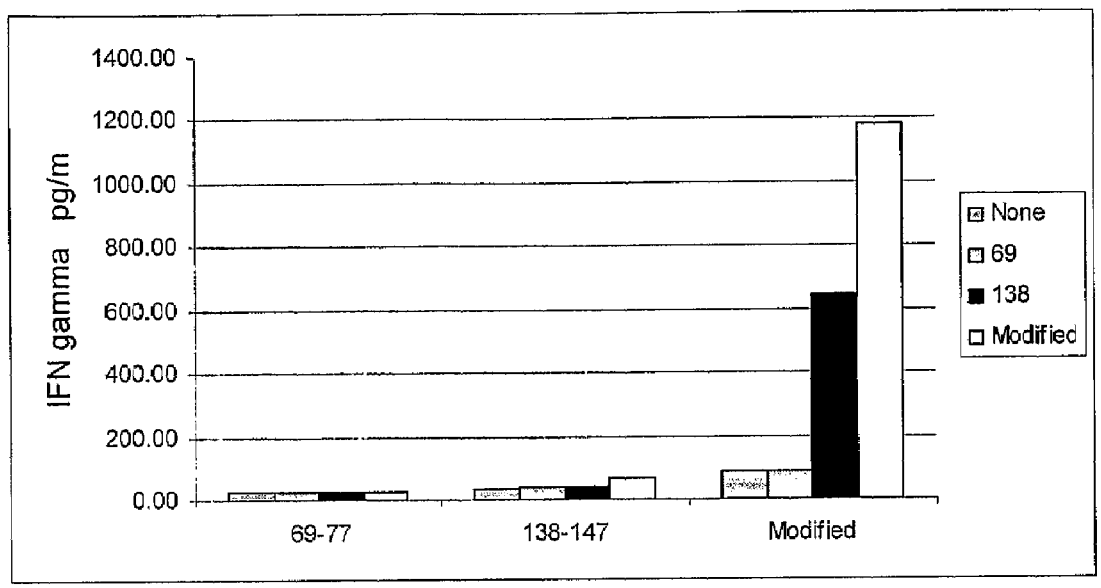
FIG. 21 shows an Elispot assay of mice immunized with wild type (SEQ ID NO: 1) or modified (SEQ ID NO: 9) E 138-147 peptides. The data shows that mice immunized with the wild type peptide failed to elicit an immune response to either the wild type (SEQ ID NO: 1) or the modified (SEQ ID NO: 9) E2 peptides. In contrast, mice immunized with the modified peptide (SEQ ID NO: 9) were found to elicit an immune response to both the wild type (SEQ ID NO: 1) and the modified (SEQ ID NO: 9) E2 peptides. Thus, the modified peptide (SEQ ID NO: 9) is more immunogenic.

The new peptide (SEQ ID NO: 9) was also found to have a higher HLA.A2 binding affinity (FIG. 20) than the unmodified E138-147 peptide (SEQ ID NO: 1). The new peptide (SEQ ID NO: 9) was additionally found to be more immunogenic than the unmodified E138-147 peptide (SEQ ID NO: 1) (FIG. 21). The new peptide (SEQ ID NO: 9) also was found to have a motif to bind HLA.A3 and HLA.A1, as shown in Table 6.

TABLE 6

|  | Peptide: YICEEASVTV (SEQ ID NO: 1) | Peptide: YLAEEASVTV (SEQ ID NO: 9) |
| --- | --- | --- |
| HLA-A 01 | 1 | 2 |
| HLA-A 0201 | 26 | 30 |
| HLA-A 00202 | 0 | 0 |
| HLA-A 03 | 17 | 20 |
| HLA-A 26 | 7 | 3 |
| HLA-A 6801 | 9 | 8 |

All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of treating a persistent human papillomavirus infection in a subject comprising administering to the subject:
   (a) a prime immunization comprising an HPV virus like particle comprising a first HPV E2 polypeptide; and
   (b) at least one boost immunization comprising a second HPV E2 polypeptide having a CTL epitope;
   wherein a CD40 agonist and a GM-CSF agent are administered in conjunction with at least one of said prime immunization or said boost immunization and said CD40 agonist and GM-CSF agent act synergistically to enhance an immune response to said first or second HPV E2 polypeptides.

2. The method of claim 1 wherein said CTL epitope is selected from the group consisting of:
   E2 138-147 (YICEEASVTV) [SEQ ID NO: 1];
   E2 69-77 (ALQAIELQL) [SEQ ID NO: 2]; and
   E2 138-147 modified (YLAEEASVTV) [SEQ ID NO: 9].

3. The method of claim 1, wherein a memory CTL response of greater than five years is obtained.

4. The method of claim 1, wherein the subject is a human subject.

5. The method of claim 1, wherein the subject is a human subject having a condition selected from the group consisting of CIN, VAIN, VIN, and AIN.

6. The method of claim 1, wherein said second HPV E2 polypeptide comprises HLA-A2 binding activity.

7. The method of claim 1, wherein the CD40 agonist is an anti-CD40 antibody, or fragment thereof.

8. The method of claim 1, wherein the HPV virus like particle further comprises an E7 polypeptide.

9. The method of claim 1, wherein the first E2 polypeptide is contained on the same polypeptide chain as the HPV L2 protein.

10. A method of treating a persistent human papillomavirus infection in a subject comprising administering to the subject;
    (a) a prime immunization comprising a first E2 polypeptide having a CTL epitope; and
    (b) at least one boost immunization comprising an HPV virus like particle comprising a second E2 polypeptide having a CTL epitope;
    wherein a CD40 agonist and a GM-CSF agent are administered in conjunction with one of said prime immunization or said boost immunization and said CD40 agonist and GM-CSF agent act synergistically to enhance an immune response to said first or second HPV E2 polypeptides.

11. The method of claim 10 wherein said CTL epitope is selected from the group consisting of:
    E2 138-147 (YICEEASVTV) [SEQ ID NO: 1];
    E2 69-77 (ALOAJELOL) [SEQ ID NO: 2]; and
    E2 138-147 modified (YLAEEASVTV) [SEQ ID NO: 9].

12. The method of claim 10, wherein a memory CTL response of greater than five years is obtained.

13. The method of claim 10, wherein the subject is a human subject.

14. The method of claim 10, wherein the subject is a human subject having a condition selected from the group consisting of CIN, VAIN, VIN, and AIN.

15. The method of claim 10, wherein said first HPV E2 polypeptide comprises HLA-A2 binding activity.

16. The method of claim 10, wherein the CD40 agonist is an anti-CD40 antibody, or fragment thereof.

17. The method of claim 10, wherein the HPV virus like particle further comprises an E7 polypeptide.

18. The method of claim 1, wherein the second E2 polypeptide is contained on the same polypeptide chain as the HPV L2 protein.

19. A method of treating a persistent human papillomavirus infection in a subject comprising administering to the subject an immunization comprising an E2 polypeptide comprising a CTL epitope selected from the group consisting of:
    E2 138-147 (YICEEASVTV) [SEQ ID NO: 1];
    E2 69-77 (ALQAIELQL) [SEQ ID NO: 2]; and
    E2 138-147 modified (YLAEEASVTV) [SEQ ID NO: 9],
    wherein said polypeptide is administered to the subject in conjunction with a CD40 agonist and a GM-CSF agent and said CD40 agonist and GM-CSF agent act synergistically to enhance an immune response to said E2 polypeptide.

20. The method of claim 19, further comprising the step of administering to the subject a boost immunization comprising an E2 polypeptide comprising a CTL epitope.

* * * * *

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: synthetic peptide

<400> SEQUENCE: 1

Tyr Ile Cys Glu Glu Ala Ser Val Thr Val
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Ala Leu Gln Ala Ile Glu Leu Gln Leu
 1               5

<210> SEQ ID NO 3
<211> LENGTH: 38
<212> TYPE: DNA
<213> ORGANISM: Artificial Sequence
<220> FEATURE:
<223> OTHER INFORMATION: synthetic primer

<400> SEQUENCE: 3
ggactagttt agatcgatac atctgaaaaa aaatatgg                          38

<210> SEQ ID NO 4
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 4

Arg Ala His Tyr Asn Ile Val Thr Phe
 1               5

<210> SEQ ID NO 5
<211> LENGTH: 10
<212> TYPE: PRT
<213> ORGANISM: Artificial Sequence
<220> FEATURE:
<223> OTHER INFORMATION: synthetic peptide

<400> SEQUENCE: 5

Tyr Met Leu Asp Leu Gln Pro Glu Thr Thr
 1               5                  10

<210> SEQ ID NO 6
<211> LENGTH: 8
<212> TYPE: PRT
<213> ORGANISM: Artificial Sequence
<220> FEATURE:
<223> OTHER INFORMATION: synthetic peptide

<400> SEQUENCE: 6

Thr Leu Gly Ile Val Cys Pro Ile
 1               5

<210> SEQ ID NO 7
<211> LENGTH: 10
<212> TYPE: PRT
<213> ORGANISM: Artificial Sequence
<220> FEATURE:
<223> OTHER INFORMATION: synthetic peptide

<400> SEQUENCE: 7

Arg Leu Asn Val Cys Gln Asp Lys Ile Leu
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Thr Leu Gln Asp Val Ser Leu Glu Val
 1               5

<210> SEQ ID NO 9
<211> LENGTH: 10
<212> TYPE: PRT
<213> ORGANISM: Artificial Sequence
<220> FEATURE:
<223> OTHER INFORMATION: synthetic peptide

<400> SEQUENCE: 9

Tyr Leu Ala Glu Glu Ala Ser Val Thr Val
 1               5                  10
```